United States Patent
Oshima et al.

(10) Patent No.: US 8,262,183 B2
(45) Date of Patent: Sep. 11, 2012

(54) CAPACITIVE LOAD DRIVING DEVICE AND FLUID EJECTION DEVICE

(75) Inventors: Atsushi Oshima, Shiojiri (JP); Kunio Tabata, Shiojiri (JP); Hiroyuki Yoshino, Matsumoto (JP); Shinichi Miyazaki, Suwa (JP); Noritaka Ide, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/072,444

(22) Filed: Mar. 25, 2011

(65) Prior Publication Data

US 2011/0234702 A1    Sep. 29, 2011

(30) Foreign Application Priority Data

Mar. 26, 2010 (JP) .................................. 2010-072406

(51) Int. Cl.
*B41J 29/38* (2006.01)
(52) U.S. Cl. ............................... 347/10; 347/9; 327/112
(58) Field of Classification Search ................. 347/9, 10, 347/54; 327/108–112, 387–388, 390–391
See application file for complete search history.

(56) References Cited

U.S. PATENT DOCUMENTS

| | | | |
|---|---|---|---|
| 4,531,096 A | | 7/1985 | Yokoyama |
| 7,259,603 B2 * | | 8/2007 | Gibson et al. ................. 327/170 |
| 7,880,539 B2 | | 2/2011 | Tabata |
| 2002/0097285 A1 | | 7/2002 | Ishizaki |
| 2005/0231179 A1 | | 10/2005 | Ishizaki |
| 2007/0057721 A1 | | 3/2007 | Risbo et al. |
| 2007/0079710 A1 | | 4/2007 | Ishizaki |
| 2007/0165074 A1 | | 7/2007 | Ishizaki |
| 2008/0198191 A1 | | 8/2008 | Oshima et al. |
| 2008/0218545 A1 | | 9/2008 | Oshima et al. |
| 2009/0066739 A1 | | 3/2009 | Tabata et al. |
| 2009/0140780 A1 | | 6/2009 | Miyazaki et al. |
| 2009/0155488 A1 | | 6/2009 | Nakano et al. |

(Continued)

FOREIGN PATENT DOCUMENTS

EP          1980400          10/2008

(Continued)

OTHER PUBLICATIONS

Rojas-Gonzalez et al. "Low-Power High-Efficiency Class D Audio Power Amplifiers" IEEE Journal of Solid-State Circuits, IEEE Service Center, Piscataway, NJ, USA, Col. 44, No. 12, Dec. 1, 2009.

(Continued)

*Primary Examiner* — Juanita D Jackson
(74) *Attorney, Agent, or Firm* — Workman Nydegger

(57) ABSTRACT

A capacitive load driving device includes a drive waveform generator adapted to generate a drive waveform signal, a subtraction section adapted to output a differential signal between the drive waveform signal and two feedback signals, a modulator adapted to perform pulse modulation on the differential signal to obtain a modulated signal; a digital power amplifier adapted to power-amplify the modulated signal to obtain an amplified digital signal, a low pass filter including an inductor and a capacitor, and adapted to smooth the amplified digital signal to obtain a drive signal of a capacitive load, a first feedback circuit adapted to feedback the drive signal to the subtraction section as a first feedback signal, and a second feedback circuit adapted to set forward a phase of the drive signal and to feed back the drive signal to the subtraction section as a second feedback signal.

16 Claims, 21 Drawing Sheets

U.S. PATENT DOCUMENTS

| | | |
|---|---|---|
| 2009/0160891 A1 | 6/2009 | Ishizaki |
| 2009/0303271 A1 | 12/2009 | Tabata et al. |
| 2010/0045714 A1 | 2/2010 | Ishizaki |
| 2010/0091059 A1 | 4/2010 | Oshima et al. |
| 2011/0109674 A1 | 5/2011 | Oshima |

FOREIGN PATENT DOCUMENTS

| | | |
|---|---|---|
| JP | 62-155698 | 7/1987 |
| JP | 11-204850 | 7/1999 |
| JP | 2002-210958 | 7/2002 |
| JP | 2005-329710 | 12/2005 |
| JP | 2007-096364 | 4/2007 |
| JP | 2007-168172 | 7/2007 |
| JP | 2007-190708 | 8/2007 |
| JP | 2008-087467 | 4/2008 |
| JP | 2008-132765 | 6/2008 |
| JP | 2008-153272 | 7/2008 |
| JP | 2008-200973 | 9/2008 |
| JP | 2008-283830 | 11/2008 |
| JP | 2009-131990 | 6/2009 |
| JP | 2009-152603 | 7/2009 |
| JP | 2010-046989 | 3/2010 |
| JP | 2011-088294 | 5/2011 |
| WO | 00/42702 | 7/2000 |
| WO | 2007/072945 | 6/2007 |

OTHER PUBLICATIONS

European Search Report and Written Opinion, cited in EP Application No. 111159763, mailed Jul. 26, 2011.

* cited by examiner

CAPACITIVE LOAD DRIVING DEVICE AND FLUID EJECTION DEVICE

CROSS-REFERENCE TO RELATED APPLICATIONS

This application claims the benefit of Japanese Application No. 2010-072406 filed on Mar. 26, 2010, which application is incorporated by reference in its entirety.

BACKGROUND

1. Technical Field

Embodiments of the present invention relate to a capacitive load driving device for applying a drive signal to a capacitive load, such as a piezoelectric element, to thereby drive the capacitive load. Embodiments of the invention further relate to a fluid ejection device that includes an actuator as the capacitive load and that applies the drive signal to the actuator to thereby eject a fluid.

2. Related Art

In the case of power-amplifying the drive waveform signal composed of a predetermined voltage waveform with a digital power amplifier to form a drive signal that is applied to an actuator formed of a capacitive load, a modulator performs a pulse modulation on the drive waveform signal to form a modulated signal, the digital power amplifier performs a power amplification on the modulated signal to form an amplified digital signal, and a low pass filter smoothes the amplified digital signal to form the drive signal.

If the waveform of the drive signal is important, there are some cases in which a feedback signal is formed by setting forward or advancing the phase of the drive signal. The difference value between the feedback signal and the drive waveform signal obtained by the subtraction section is used as an input signal to the modulator. According to JP-A-2005-329710 (Document 1), it is arranged that the output of the low pass filter composed of a quadratic low-pass filter, namely the drive signal, is fed back as a first feedback signal, and at the same time, the output of the digital power amplifier, namely the amplified digital signal is made to pass through a first-order low-pass filter and is then fed back as a second feedback signal. Since the first-order low pass filter leads the quadratic low pass filter in phase, it is intended to compensate the waveform of the drive signal with the phase-leading component. It should be noted that the frequency of the pulse modulation by the modulator is called a modulation frequency or a carrier frequency.

However, since the signal, which is fed back with its phase set forward in Document 1, is not the drive signal applied to the actuator, but is the amplified digital signal as the output of the digital power amplifier, the waveform of the drive signal cannot sufficiently be compensated.

SUMMARY

An advantage of some embodiments of the invention is to provide a capacitive load driving device and a fluid ejection device capable of sufficiently compensating the waveform of the drive signal.

A capacitive load driving device according to an embodiment of the invention includes a drive waveform generator adapted to generate a drive waveform signal, a subtraction section adapted to output a differential signal between the drive waveform signal and two feedback signals, a modulator adapted to perform pulse modulation on the differential signal to form a modulated signal, a digital power amplifier adapted to power-amplify the modulated signal to obtain an amplified digital signal, a low pass filter composed mainly of an inductor and a capacitor, and adapted to smooth the amplified digital signal to obtain a drive signal of a capacitive load, a first feedback circuit adapted to feedback the drive signal to the subtraction section as a first feedback signal, and a second feedback circuit adapted to set a phase of the drive signal forward and to feed back the drive signal to the subtraction section as a second feedback signal.

According to the capacitive load driving device, when performing pulse modulation on the differential signal between the drive waveform signal and the two feedback signals output from the subtraction section to obtain the modulated signal, performing the power amplification by the digital power amplifier on the modulated signal to obtain the amplified digital signal, and smoothing the amplified digital signal by the low pass filter to obtain the drive signal of the capacitive load, by feeding back the drive signal itself to the subtraction section as the first feedback signal, and at the same time, setting the phase of the drive signal forward and feeding it back to the subtraction section as the second feedback signal, the proportional and differential feedback of the drive signal becomes possible, and the waveform of the drive signal can sufficiently be compensated.

It is also possible to provide a current detector connected to the capacitor of the low pass filter The second feedback circuit feeds back an output of the current detector to the subtraction section as the second feedback signal.

According to this capacitive load driving device, because the current of the capacitor of the low pass filter, whose phase leads the phase of the drive signal composed of a voltage signal, can be fed back to the subtraction section as the second feedback signal, it is possible to feedback the second feedback signal such that the second feedback signal is capable of sufficiently compensating the waveform of the drive signal with a simple configuration.

It is also possible to provide a second capacitor to be connected to an output side of the low pass filter and having a capacity smaller than a capacity of the capacitor of the low pass filter, and a current detector connected to the second capacitor. The second feedback circuit feeds back an output of the current detector to the subtraction section as the second feedback signal.

According to this capacitive load driving device, because the current of the capacitor of the low pass filter, whose phase leads the phase of the drive signal composed of a voltage signal, can be fed back to the subtraction section as the second feedback signal, it is possible to feedback the second feedback signal capable such that the second feedback signal is capable of sufficiently compensating the waveform of the drive signal. Further, by using the second capacitor having a small capacitance, namely a large impedance, the power loss can be reduced.

It is also possible to further provide an inverse filter intervening between the drive waveform generator and the subtraction section, and capable of obtaining or outputting a desired drive signal even in the case in which frequency characteristics of a capacitance of the low pass filter and the capacitive load vary in accordance with the number of capacitive loads to be driven.

According to this capacitive load driving device, by correcting the drive waveform signal in accordance with the number of capacitive loads to be driven using the inverse filter, the compensation of the drive signal by the first feedback signal can be reduced. Thus, the gain margin and the phase margin of the open-loop characteristics of the path from the subtraction section to the drive signal can be increased to thereby make the capacitive load driving device operate more stably.

The modulator can be provided with a comparison section adapted to compare the differential signal of the subtraction section and a triangular wave signal to thereby convert the drive signal into the modulated signal.

According to this capacitive load driving device, the modulated signal can be obtained from a simple configuration.

It is possible that the modulator is provided with an integration section and a comparison section adapted to convert an output of the integration section into the modulated signal. The integration section is configured to integrate a difference between the differential signal of the subtraction section and the modulated signal, and then output the result of the integration.

According to this capacitive load driving device, by feeding back the modulated signal, the waveform accuracy of the drive signal can further be improved.

It is possible that the modulator is provided with an integration section and a comparison section adapted to convert an output of the integration section into the modulated signal. The integration section is configured to integrate a difference between the differential signal of the subtraction section and the amplified digital signal, and then output the result of the integration.

According to this capacitive load driving device, by feeding back the amplified digital signal without any phase-lag, it is possible to make the capacitive load driving device operate stably. Because the amplified digital signal including the variation in the power supply voltage of the digital power amplifier is fed back, it is possible to compensate the variation in the power supply voltage of the digital power amplifier to thereby further improve the waveform accuracy of the drive signal.

A fluid ejection device according to another embodiment of the invention includes the capacitive load driving device according to the above embodiments of the invention, and an actuator as the capacitive load, where the capacitive load driving device drives the actuator to eject a fluid.

According to the fluid ejection device of this embodiment of the invention, the waveform of the drive signal for the actuator as the capacitive load can be sufficiently compensated, and thus the fluid ejection with higher accuracy becomes possible.

BRIEF DESCRIPTION OF THE DRAWINGS

Embodiments of the invention will be described with reference to the accompanying drawings, where like numbers reference like elements.

FIG. 9A is a frequency characteristics chart, and FIG. 9B is an open-loop characteristics chart.

FIG. 11A is a frequency characteristics chart, and FIG. 11B is an open-loop characteristics chart.

FIG. 14A is a frequency characteristics chart, and FIG. 14B is an open-loop characteristics chart.

DESCRIPTION OF EXEMPLARY EMBODIMENTS

Then, as a first embodiment of the invention, a capacitive load driving device applied to an inkjet printer is disclosed.

Figure 1:
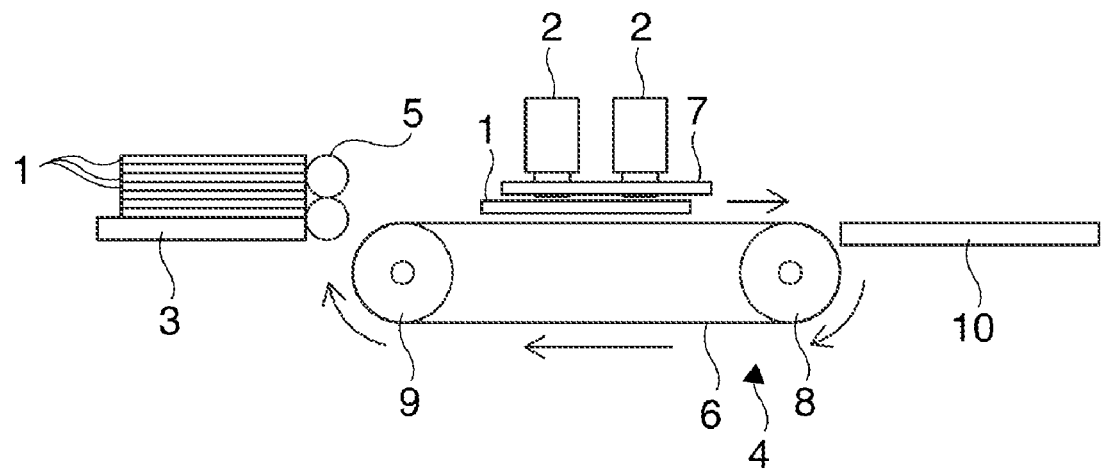
FIG. 1 is a front view of a schematic configuration illustrating an inkjet printer using a capacitive load driving device in a first embodiment of the invention.

FIG. 1 is a schematic configuration diagram of the inkjet printer according to the present embodiment. In FIG. 1, the inkjet printer may be a line head inkjet printer in which a print medium 1 is conveyed in the arrow direction from the left to the right of the drawing, and printed in a printing area that is midway of the conveying path.

Figure 2:
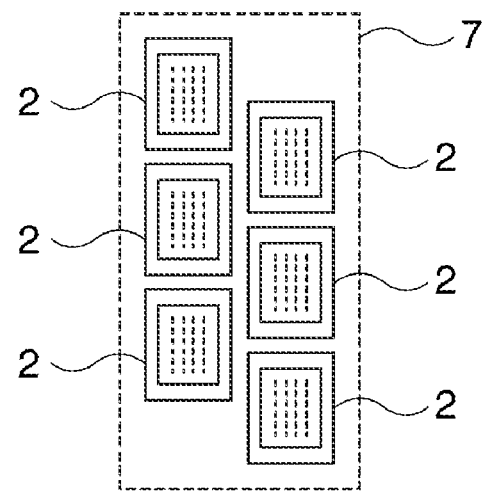
FIG. 2 is a plan view of the vicinity of inkjet heads used in the inkjet printer shown in FIG. 1.

The reference numeral 2 shown in FIG. 1 denotes a plurality of inkjet heads disposed above a conveying line of the print medium 1. The inkjet heads 2 are arranged in a direction intersecting with the print medium conveying direction in two lines arranged in the print medium conveying direction, and are fixed individually to a head fixing plate 7. Each of the inkjet heads 2 is provided with a number of nozzles on the lowermost surface thereof. The lowermost surface is called a nozzle surface. As shown in FIG. 2, the nozzles are arranged so as to form lines in a direction intersecting with the print medium conveying direction color by color in accordance with the colors of the ink to be ejected. The lines are called nozzle lines and the direction of the lines is called a nozzle line direction. The nozzle lines of all of the inkjet heads 2 arranged in a direction intersecting with the print medium conveying direction constitute a line head covering the overall width of the print medium in a direction intersecting with the conveying direction of the print medium 1.

The inkjet heads 2 are supplied with, for example, ink of four colors (e.g., yellow (Y), magenta (M), cyan (C), and black (K)) from respective ink tanks not shown via ink supply tubes. A necessary amount of ink is ejected simultaneously from the nozzles, which are provided to the inkjet heads 2, to necessary positions, thereby forming fine dots on the print medium 1. By executing the above for each of the colors, one-pass printing can be performed by making the print medium 1, which is conveyed by the conveying section 4, pass through once. In the present embodiment, a piezoelectric driving method may be adopted as the method of ejecting the ink from the nozzles of the inkjet heads 2. In the piezoelectric driving method, when a drive signal is applied to a piezoelectric element as an actuator, a diaphragm in a pressure chamber is displaced to cause the capacity of the pressure chamber to vary. The ink in the pressure chamber is ejected from the nozzle due to the pressure variation caused at that time. By controlling the wave height and the voltage variation gradient of the drive signal, it becomes possible to control the ejection amount of the ink. It should be noted that embodiments of the invention can also be applied to ink ejection methods other than the piezoelectric driving method in a similar manner.

Under the inkjet heads 2, there is disposed the conveying section 4 for conveying the print medium 1 in the conveying direction. The conveying section 4 is configured by winding a conveying belt 6 around a drive roller 8 and a driven roller 9. An electric motor (not shown) is coupled to the drive roller 8. In the inside of the conveying belt 6, an adsorption device (not shown) is disposed for adsorbing the print medium 1 on the surface of the conveying belt 6. As the adsorption device there is used. For example, an air suction device for suctioning the print medium 1 to the conveying belt 6 with negative pressure, or an electrostatic adsorption device for adsorbing the print medium 1 to the conveying belt 6 with electrostatic force. Therefore, when a feed roller 5 feeds just one sheet of the print medium 1 to the conveying belt 6 from a feeder section 3, and then the electric motor rotationally drives the drive roller 8, the conveying belt 6 is rotated in the print medium conveying direction, and the print medium 1 is conveyed while being adsorbed to the conveying belt 6 by the adsorption device. While conveying the print medium 1, printing is performed by ejecting the ink from the inkjet heads 2. The print medium 1 on which printing has been performed is ejected to a paper ejection section 10 disposed on the downstream side in the conveying direction. It should be noted that a print reference signal output device composed of, for example, a linear encoder is attached to the conveying belt 6. A drive circuit described later outputs a drive signal to the actuators in accordance with the pulse signal output from the print reference signal output device and corresponding to the required resolution, thereby ejecting the ink of predetermined colors at predetermined positions on the print medium 1 to form dots. In this manner, a predetermined image is drawn on the print medium 1 with the dots.

Figure 3:
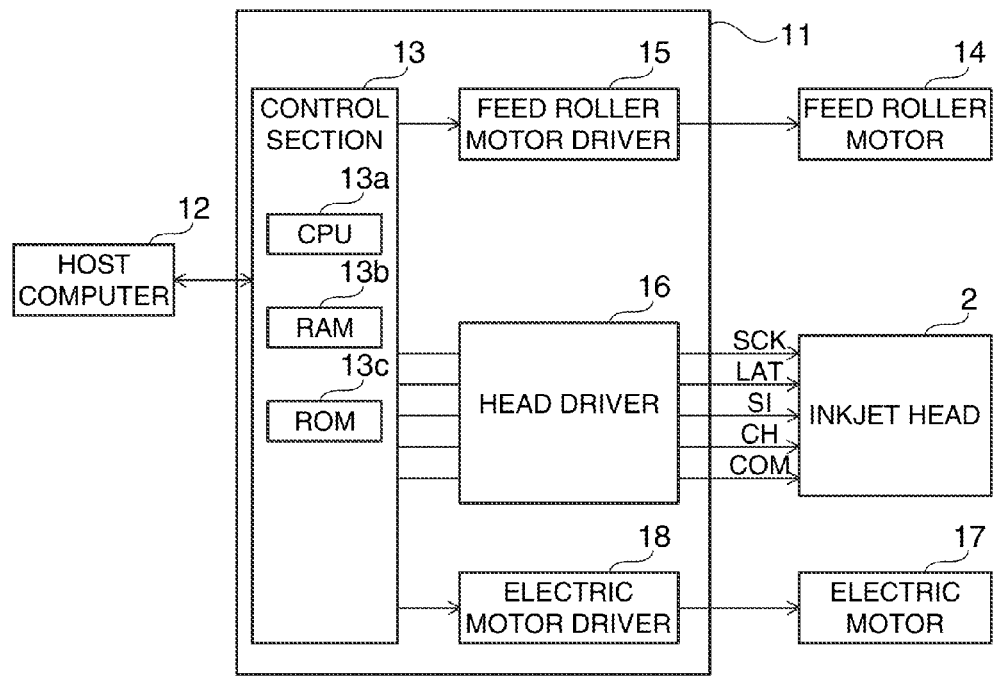
FIG. 3 is a block diagram of a control device of the inkjet printer shown in FIG. 1.

Inside the inkjet printer according to the present embodiment, there is disposed a control device 11 for controlling the inkjet printer. As shown in FIG. 3, the control device 11 is provided with a control section 13 composed of a computer system for reading the print data input from the host computer 12, and then performing an arithmetic process such as a printing process based on the print data. The control device 11 is provided with a feed roller motor driver 15 for controlling drive of the feed roller motor 14 coupled to the feed roller 5 described above. The control device 11 is configured to include a head driver 16 for controlling or driving the inkjet head 2, and an electric motor driver 18 for controlling or driving the electric motor 17 coupled to the drive roller 8.

The control section 13 is provided with a central processing unit (CPU) 13a for executing various types of processes such as a printing process. The control section 13 is provided with a random access memory (RAM) 13b for temporarily storing the print data input thereto and various kinds of data used in performing the printing process of the print data, and for temporarily developing a program, for example, for the printing process. The control section 13 is provided with a read-only memory (ROM) 13c composed of a nonvolatile semiconductor memory and for storing, for example, the control program executed by the CPU 13a. When the control section 13 obtains the print data (image data) from the host computer 12, the CPU 13a executes a predetermined process on the print data to obtain nozzle selection data (drive pulse selection data) representing which nozzle the ink is ejected from and/or how much ink is ejected from the nozzle. Based on the print data, the drive pulse selection data, and input data from various sensors, drive signals and control signals are output to the feed roller motor driver 15, the head driver 16, and the electric motor driver 18. In accordance with these drive signals and control signals, the feed roller motor 14, the electric motor 17, actuators inside the inkjet head 2, and so on operate individually, thus feeding and conveying the print medium 1 and ejecting ink on the print medium 1. Thus, the printing processes to the print medium 1 are executed. It should be noted that the constituents inside the control section 13 are electrically connected to each other via a bus not shown in the drawings.

Figure 4:
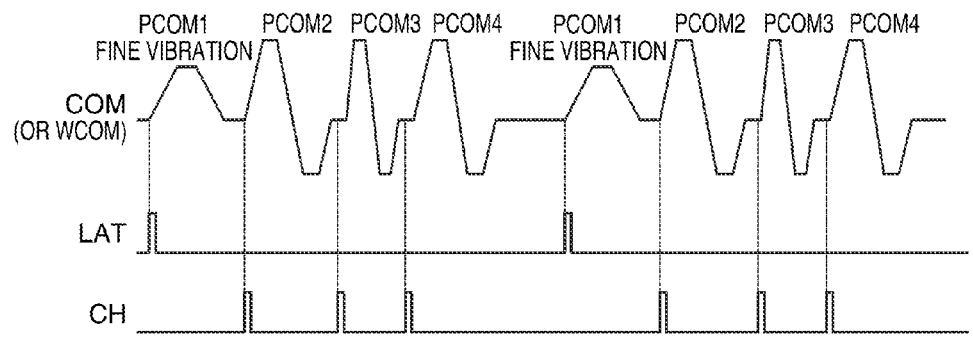
FIG. 4 is an illustrative diagram of a drive signal of an actuator composed of a capacitive load.

FIG. 4 shows an example of the drive signal COM supplied from the head driver 16 in the control device 11 to the inkjet heads 2, and for driving the actuators, each actuator composed of a piezoelectric element in one embodiment. In the present embodiment, it is assumed that the signal has a voltage varying around an intermediate voltage. The drive signal COM is formed by connecting drive pulses PCOM as a unit drive signal for driving the actuator so as to emit the ink in a time-series manner, wherein the rising section of each of the drive pulses PCOM corresponds to a stage of expanding the volume of the pressure chamber communicating with the nozzle to take in the ink, and the falling section of each of the drive pulses PCOM corresponds to a stage of reducing the volume of the pressure chamber to push out the ink. As a result of pushing out the ink, the ink is ejected from the nozzle.

By variously modifying the gradient of increase and decrease in voltage and the wave height of the drive pulse PCOM formed of trapezoidal voltage waves, the pull-in amount and the pull-in speed of the ink, and the push-out amount and the push-out speed of the ink can be modified. Thus the ejection amount of the ink can be varied to obtain the dots with respective sizes that are different from each other. Therefore, even in the case in which a plurality of drive pulses PCOM are joined in a time-series manner, it is possible to select a single drive pulse PCOM from the drive pulses, and to supply the actuator 19 with the selected drive pulse PCOM to thereby eject the ink, or to select two or more drive pulses PCOM, and to supply them to the actuator 19 to eject the ink two or more times, thereby obtaining the dots with various sizes. In other words, when the two or more droplets land on the same position before the droplets are dried, it brings substantially the same result as in the case of ejecting a larger amount of ink or a larger droplet. Thus, it is possible to increase the size of the dot. By a combination of such technologies, it becomes possible to achieve multiple tone printing. It should be noted that the drive pulse PCOM1 shown in the left end of FIG. 4 is only for pulling in the ink without pushing it out. This is called a fine vibration, and is used, for example, for preventing the ink from thickening in the nozzle without ejecting the ink.

In addition to the drive signal COM, drive pulse selection specifying data SI, representing which one of the drive pulses PCOM is to be selected based on the print data, is input from the control device shown in FIG. 3 described above to the inkjet head 2 as one of the control signals. A latch signal LAT and a channel signal CH for coupling the drive signal COM and the actuator of the inkjet head 2 to each other based on the drive pulse selection specifying data SI after inputting the nozzle selection data to all of the nozzles, and a clock signal SCK for transmitting the drive pulse selection specifying data SI to the inkjet head 2 as a serial signal are input to the inkjet head 2. It should be noted that it is hereinafter assumed that the minimum unit of the drive signal for driving the actuator 19 is the drive pulse PCOM, and the entire signal having the drive pulses PCOM joined with each other in a time-series manner is described as the drive signal COM. In other words, output of a string of drive signal COM is started in response to the latch signal LAT, and the drive pulse PCOM is output in response to each channel signal CH.

Figure 5:
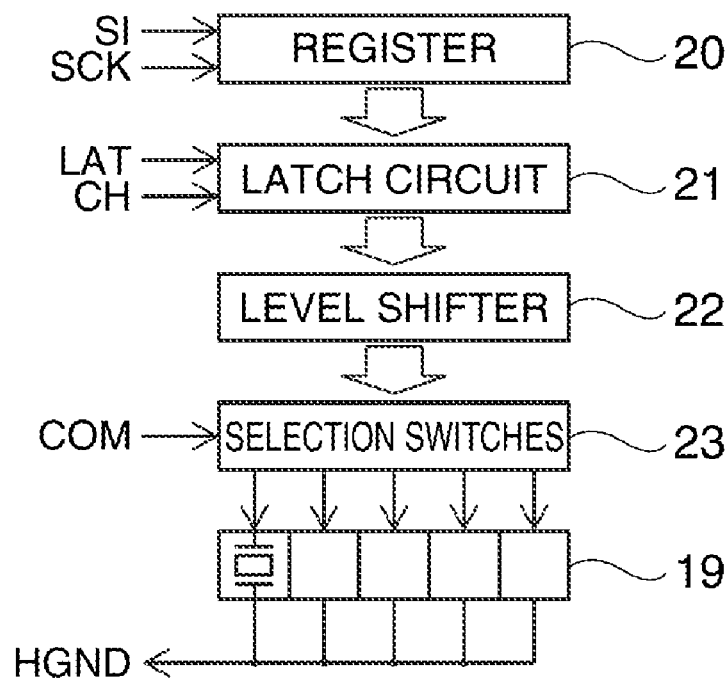
FIG. 5 is a block diagram of a switching control section.

FIG. 5 shows a specific configuration of a switching control section, which is built in the inkjet head 2 in order to supply or provide the actuator 19 with the drive signal COM (the drive pulse PCOM). The switching control section is provided with a register 20 for storing the drive pulse selection specifying data SI for designating the actuator 19, such as a piezoelectric element corresponding to the nozzle made to eject the ink, and a latch circuit 21 for temporarily storing the data of the register 20. The switching control section is configured to include a level shifter 22 for performing the level conversion on the output of the latch circuit 21, and then supplying the result to a selection switch 23, thereby coupling the drive signal COM (the drive pulse PCOM) to the actuators 19, each composed of the piezoelectric element.

The level shifter 22 converts the output of the latch circuit 21 into the voltage level that is enough for switching the selection switches 23 ON or OFF. This is because the drive signal COM (the drive pulse PCOM) has a relatively high voltage compared to the output voltage of the latch circuit 21. The operating voltage range of the selection switches 23 is also set to be high in accordance therewith. Therefore, the actuator 19 having the selection switch 23 closed by the level shifter 22, is coupled to the drive signal COM (the drive pulse PCOM) at a predetermined coupling timing based on the drive pulse selection specifying data SI. After the drive pulse selection specifying data SI of the register 20 is stored in the latch circuit 21, the subsequent print information is input to the register 20, and the stored data in the latch circuit 21 is sequentially updated in sync with the ejection timing of the ink. It should be noted that the reference symbol HGND in the drawing denotes the ground terminal for the actuators 19 such as piezoelectric elements. Further, even after the selection switch 23 separates (the selection switch is set OFF) the actuator 19 such as a piezoelectric element from the drive signal COM (the drive pulses PCOM), the input voltage of the actuator 19 is kept at the voltage applied thereto immediately before the separation. In other words, the actuator 19 composed of the piezoelectric element is a capacitive load.

Figure 6:
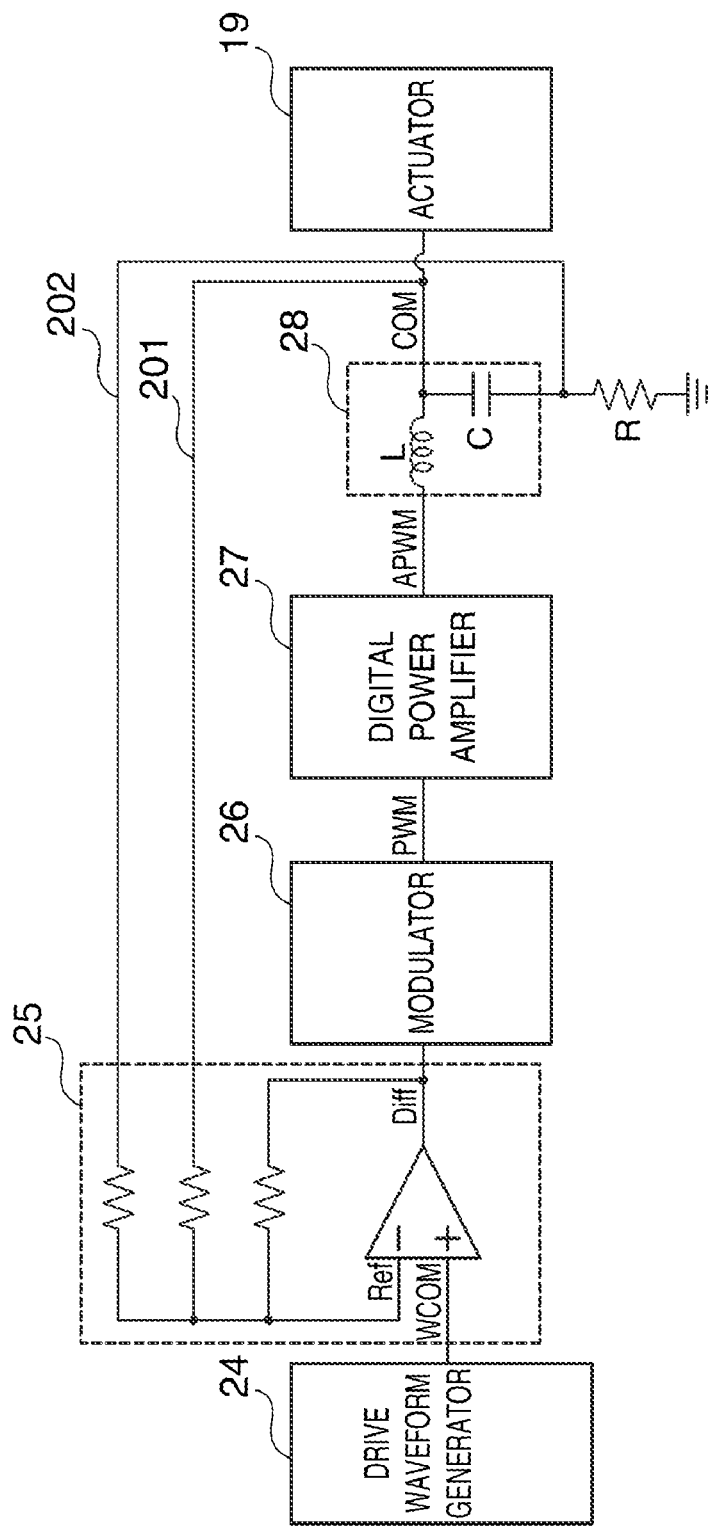
FIG. 6 is a block diagram showing an example of an actuator drive circuit.

FIG. 6 shows a schematic configuration of the drive circuit for the actuator 19. The actuator drive circuit is built inside the head driver 16 of the control device 11. The drive circuit of the present embodiment is provided with a drive waveform generator 24 for generating a drive waveform signal WCOM forming a basis of the drive signal COM (the drive pulse PCOM), namely a basis of the signal for controlling the drive of the actuator 19, based on the drive waveform data DWCOM stored previously. The drive circuit according to the present embodiment is provided with a subtraction section 25 for subtracting the feedback signal Ref from the drive waveform signal WCOM generated by the drive waveform generator 24 to thereby output the differential signal Diff, a modulator 26 for performing a pulse modulation on the differential signal Diff output from the subtraction section 25, and a digital power amplifier 27 for performing power amplification on the modulated signal PWM on which the pulse modulation is performed by the modulator 26. The drive circuit of the present embodiment is configured to include a low pass filter 28 for smoothing the amplified digital signal APWM power-amplified by the digital power amplifier 27 to output it to the actuator 19 composed of the piezoelectric element as the drive signal COM, a first feedback circuit 201 for feeding back the drive signal COM, which is the output of the low pass filter 28, to the subtraction section 25, and a second feedback circuit 202 for setting forward or advancing the phase of the drive signal COM and then feeding it back to the subtraction section 25.

Figure 7:
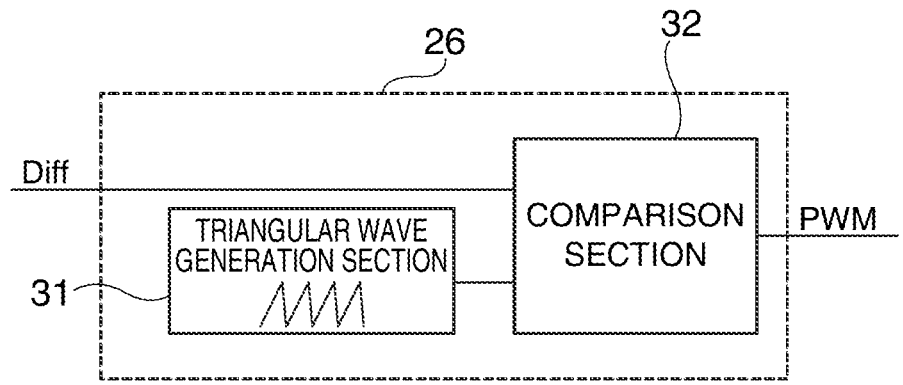
FIG. 7 is a block diagram of a modulator shown in FIG. 6.

The drive waveform generator 24 converts the drive waveform data DWCOM composed of digital data into the voltage signal, and then holds the output of the voltage signal for a predetermined sampling period. The subtraction section 25 is an ordinary analog subtraction circuit with resistors for setting proportionality factors intervening therebetween. As shown in FIG. 7, a known pulse width modulator (PWM) is used as the modulator 26. The pulse width modulator is configured to include, for example, a triangular wave generation section 31 for outputting a triangular wave signal with a predetermined frequency, and a comparison section 32 for comparing the triangular wave signal and the differential signal Diff with each other. The comparison section 32 outputs a modulated signal PWM with a pulse duty cycle in which the on-duty represents the fact that the differential signal Diff is higher than the triangular wave signal, for example. It should be noted that a well-known pulse modulator such as a pulse density modulator (PDM) can be used as the modulator 26 besides the modulator described above. The drive waveform generator 24, the subtraction section 25, and the modulator 26 can also be built with arithmetic processes. These sections can be built, for example, inside the control section 13 of the control device 11 by programming.

Figure 8:
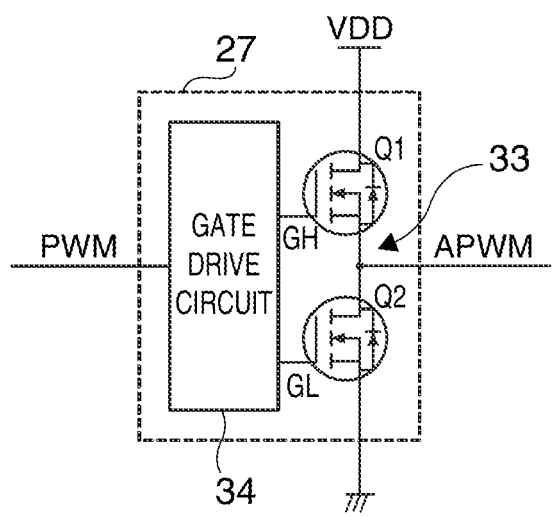
FIG. 8 is a block diagram of a digital power amplifier shown in FIG. 6.

As shown in FIG. 8, the digital power amplifier 27 is configured including a half-bridge output stage 33 formed of a high-side switching element Q1 and a low-side switching element Q2 for substantially amplifying the power. The digital power amplifier 27 includes a gate drive circuit 34 for controlling gate-source signals GH, GL of the high-side switching element Q1 and the low-side switching element Q2 based on the modulated signal PWM from the modulator 26. In the digital power amplifier 27, when the modulated signal is at the high level, the gate-source signal GH of the high-side switching element Q1 is at the high level and the gate-source signal GL of the low-side switching element Q2 is at the low level. Consequently, the high-side switching element Q1 is in the ON state and the low-side switching element Q2 is in the OFF state. As a result, the output voltage Va of the half-bridge output stage 33 becomes equal to the power supply voltage VDD. On the other hand, when the modulated signal is at the low level, the gate-source signal GH of the high-side switching element Q1 is at the low level and the gate-source signal GL of the low-side switching element Q2 is at in the high level. Consequently, the high-side switching element Q1 is in the OFF state and the low-side switching element Q2 is in the ON state. As a result, the output voltage Va of the half-bridge output stage 33 becomes 0.

In the case in which the high-side switching element Q1 and low-side switching element Q2 are driven digitally as described above, although a current flows through the switching element in the ON state, the resistance value between the drain and the source is extremely small, and therefore, the loss is very small or almost zero. Since no current flows in the switching element in the OFF state, no loss is caused. Therefore, the loss itself of the digital power amplifier 27 is extremely small, and therefore, to the digital power amplifier 27 can use small-sized switching elements such as MOS-FETs.

As shown in FIG. 6, the low pass filter 28 may be composed of a quadratic low pass filter constituted with one inductor L and one capacitor C. In the present embodiment, amplitude of the signal with the modulation frequency generated by the modulator 26, namely the frequency component of the pulse modulation, is attenuated to be removed by the low pass filter 28, and then the drive signal COM (the drive pulse PCOM) is output to the actuator 19.

As described above, the actuator 19 is provided to each of the nozzles shown in FIG. 2, and the drive signal COM (the drive pulse PCOM) is applied to the actuator 19 having the selection switch 23 shown in FIG. 5 closed, and thus the actuator provided with the drive signal COM is driven. The actuator 19 has a capacitive load, namely a capacitance. Specifically, the capacitance corresponding to the number (hereinafter also described as the number of driven actuators) of actuators to be driven is connected to the low pass filter 28 in parallel to the capacitor C of the low pass filter 28. Naturally, if the number of driven actuators varies, the frequency characteristics of the filter composed of the low pass filter 28 and the capacitances of the actuators 19 to be driven also vary. In order to compensate the variation in the frequency characteristics of the filter composed of the low pass filter 28 and the capacitances of the actuators 19 to be driven, the actuator drive circuit shown in FIG. 6 is provided with a first feedback circuit 201 for feeding back the drive signal COM (the drive pulse PCOM) directly to the subtraction section 25 as a first feedback signal. The actuator drive circuit shown in FIG. 6 is also provided with a second feedback circuit 202 for setting forward or advancing the phase of the drive signal COM (the drive pulse PCOM) and then feeding the resulting signal back to the subtraction section 25 as a second feedback signal.

The second feedback circuit 202 detects the current of the capacitor C of the low pass filter 28 with a current detector, and then sets the output of the current detector to the second feedback signal. The current detector is composed of a grounded resistor R in one example. Since the current leads the voltage in phase, and the drive signal COM (the drive pulse PCOM) is a trapezoidal wave voltage signal as described above, the current signal of the capacitor C thus detected leads the drive signal COM (the drive pulse PCOM) in phase. The capacitor C and the grounded resistor R constitute a first-order high pass filter. As described above, by using the first feedback signal composed of the drive signal COM (the drive pulse PCOM) and the second feedback signal obtained by setting forward or advancing the phase of the drive signal COM (the drive pulse PCOM), the proportional and differential feedback of the drive signal COM (the drive pulse PCOM) becomes possible. Thus it becomes possible to compensate the frequency characteristics of the filter composed of the low pass filter 28 and the capacitances of the actuators 19 to be driven due to the variation in the number of driven actuators. It should be noted that although the quadratic low pass filter without the damping resistor intervening therebetween such as the low pass filter 28 of the present embodiment has a resonant property, it is also possible to compensate the resonant property of the quadratic low pass filter constituting the low pass filter 28 by feeding back the first feedback signal and the second feedback signal as disclosed herein.

Figure 9A:
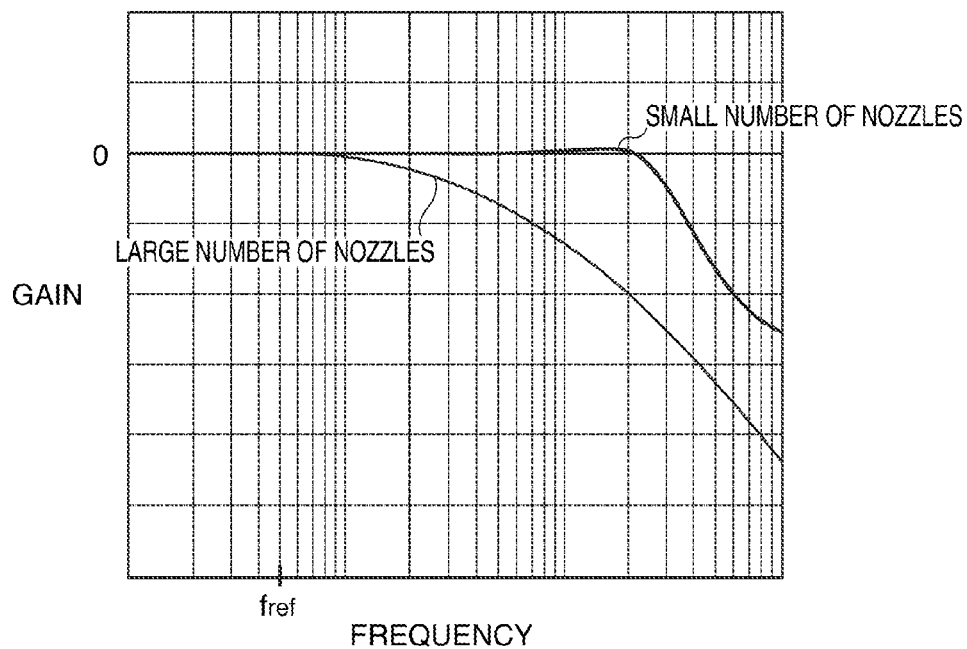
FIGS. 9A and 9B are illustrative diagrams of the action of the drive circuit shown in FIG. 6, where
Figure 9B:
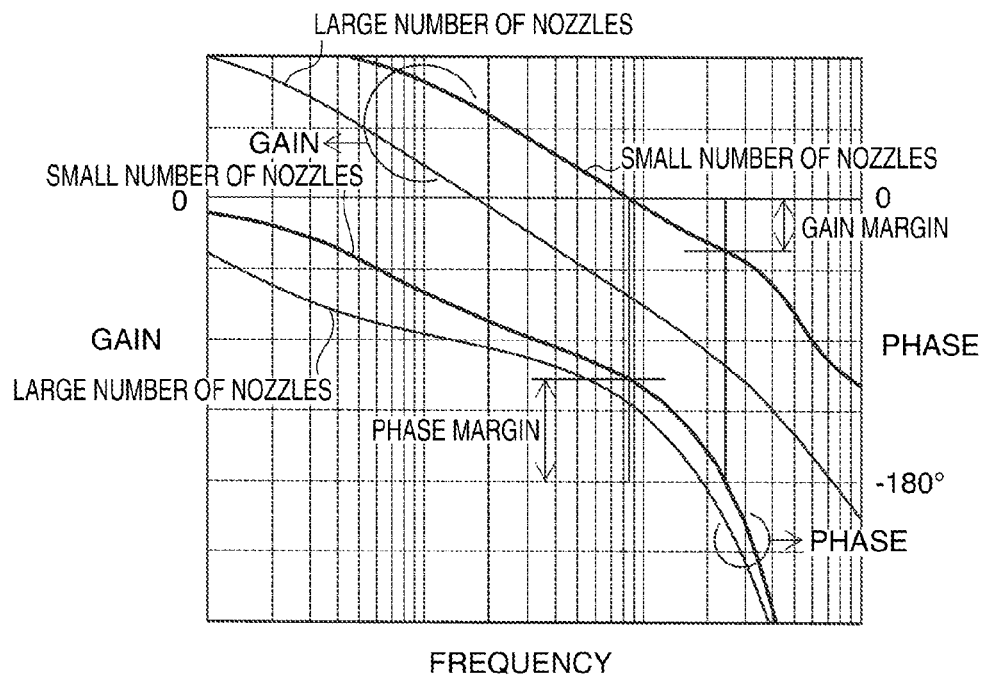

FIGS. 9A and 9B show the frequency characteristics of the actuator drive circuit of the present embodiment provided with the first feedback circuit 201 and the second feedback circuit 202. FIG. 9A shows the frequency characteristics of the filter composed of the low pass filter 28 and the capacitances of the actuators 19 to be driven, namely the drive signal COM (the drive pulse PCOM), and the reference symbol $f_{ref}$ in the drawing denotes the predetermined frequency necessary for preventing the waveform of the drive signal COM (the drive pulse PCOM) from being distorted. Therefore, it is required to set the gain of the filter to 0 dB in at least the frequency band equal to or lower than the predetermined frequency $f_{ref}$. As is illustrated in the drawing, although there is a tendency that the gain in the higher frequency band is lowered as the number (the number of nozzles in the drawing) of driven actuators increases, the gain of the filter is set to approximately 0 dB in the frequency band equal to or lower than the predetermined frequency $f_{ref}$.

FIG. 9B shows the open-loop characteristics of the actuator drive circuit shown in FIG. 6. The open-loop characteristics of the drive circuit provided with the feedback corresponds to the frequency characteristics of the path from the feedback input, namely the input side of the subtraction section 25 in the present embodiment, to the actuator 19, where the gain higher than 0 dB means that the output is larger than the feedback input, and the gain lower than 0 dB means that the output is smaller than the feedback input. The phase of $-180°$ means the inverted signal of the input. In the open-loop characteristics of the drive circuit provided with the feedback if the phase is $-180°$, and the gain is equal to or higher than 0 dB, an infinite gain is caused that results in oscillation. In other words, the system becomes unstable. Therefore, in order to check the stability of the system, it is sufficient to measure the phase margin, which is the difference from the phase of $-180°$ at the gain of 0 dB, and, by contraries, the gain margin, which is the difference from the gain of 0 dB at the phase of $-180$. In the present embodiment, although there is a tendency that both the gain margin and the phase margin are small in the case in which the number of driven actuators is small, the margins are still enough for the system to operate stably.

Figure 10:
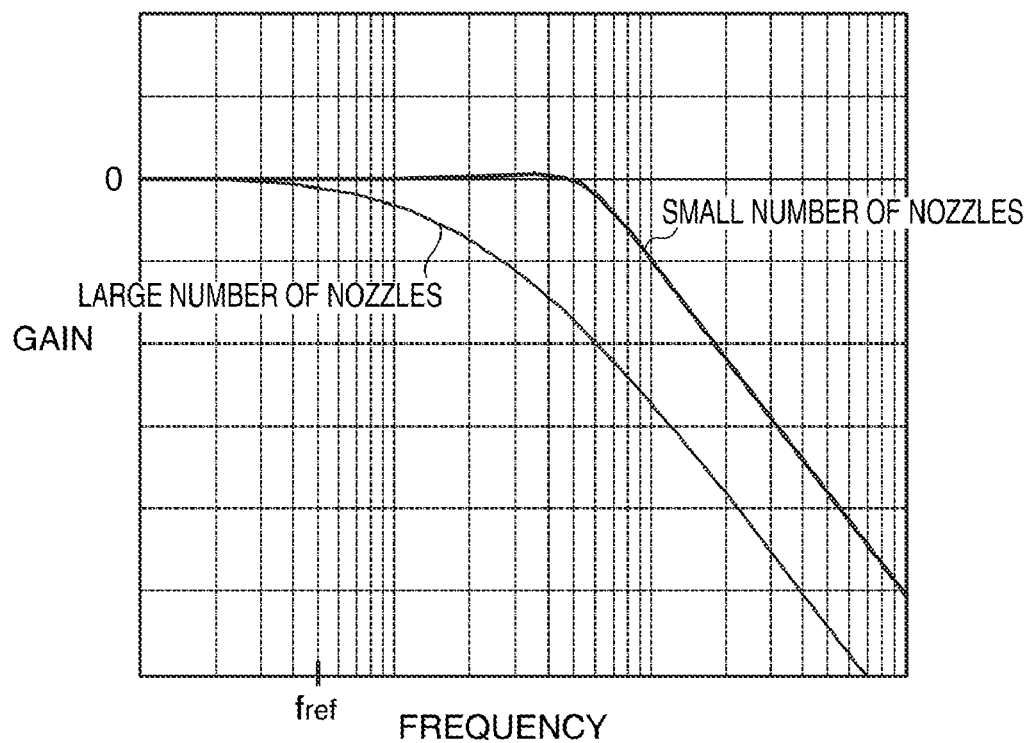
FIG. 10 is a frequency characteristics chart of the drive circuit in the case of eliminating a feedback circuit.
Figure 11A:
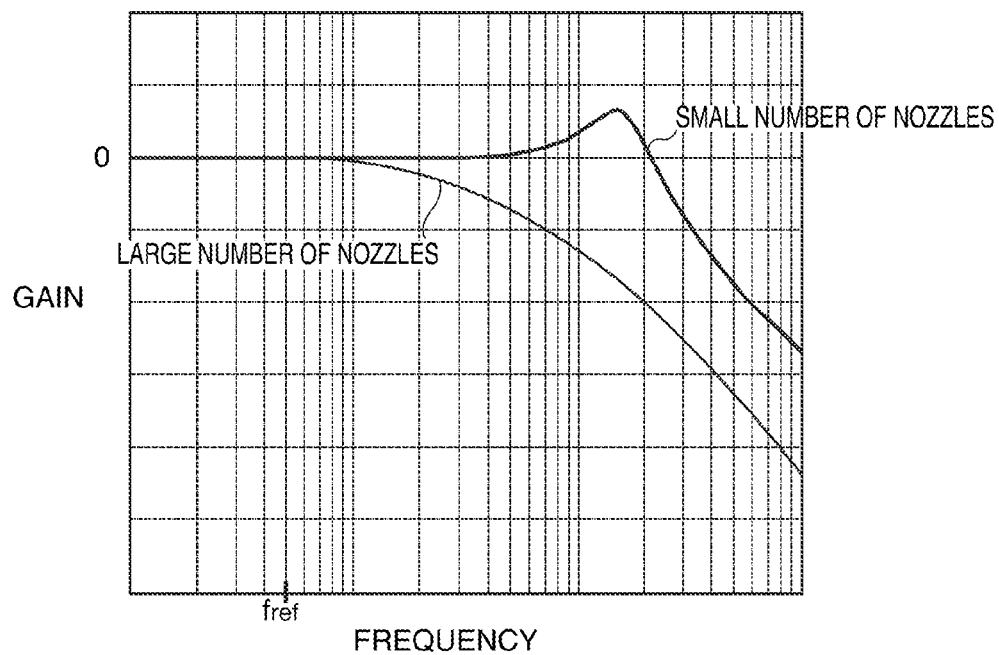
FIGS. 11A and 11B are explanatory diagrams of the action of the drive circuit shown in FIG. 6 without the second feedback circuit, where
Figure 11B:
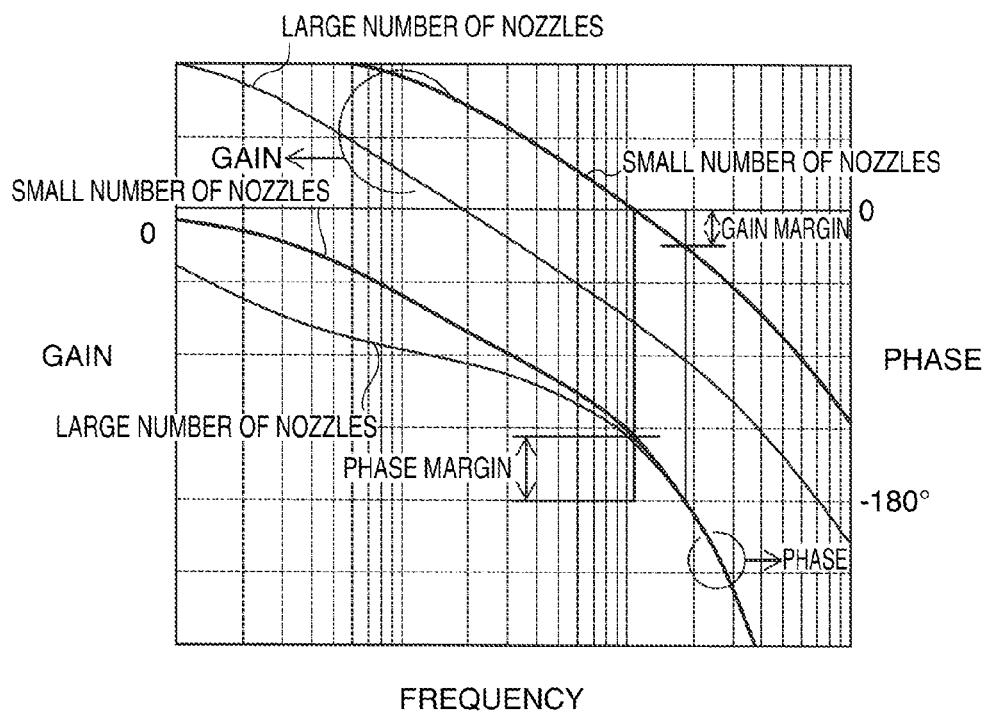

FIG. 10 shows the frequency characteristics of the filter without the feedback of the first feedback signal and the feedback of the second feedback signal, in a manner of speaking, the filter composed of the low pass filter 28 and the capacitances of the actuators to be driven (with the damping resistor intervening therebetween, which prevents the resonance). Similar to the case of FIG. 9A, there is a tendency that the larger the number of driven actuators is, the lower the gain in the higher frequency band becomes. However, in this case, the gain becomes lower than 0 dB at the predetermined frequency fref described above, and the waveform of the drive signal COM (the drive pulse PCOM) is distorted (the high frequency band component is eliminated). FIGS. 11A and 11B show the frequency characteristics in the case of performing the feedback using only the first feedback signal. In the frequency characteristics of the filter composed of the low pass filter 28 and the capacitances of the actuators 19 to be driven, namely the drive signal COM (the drive pulse PCOM) shown in FIG. 11A, the gain at the predetermined frequency $f_{ref}$ in the case in which the number of driven actuators is large is improved. However, in the open-loop characteristics shown in FIG. 11B, both the gain margin and the phase margin are reduced compared to the open-loop characteristics shown in FIG. 9B described above. The margins are not enough for the system to operate stably.

In the capacitive load driving device and the inkjet printer according to the present embodiment, when the drive signal COM (the drive pulse PCOM) is applied to the actuator 19 composed of the capacitive load, such as the piezoelectric element, the capacity of the pressure chamber of the inkjet head 2 is reduced to thereby eject the ink in the pressure chamber. When printing the print medium 1 with the ink thus ejected, the pulse modulation is performed on the differential signal Diff between the drive waveform signal WCOM output from the subtraction section 25 and the two feedback signals Ref to obtain the modulated signal PWM, the power amplification is performed by the digital power amplifier 27 on the modulated signal PWM to obtain the amplified digital signal APWM, and the amplified digital signal APWM is smoothed by the low pass filter 28 to thereby obtain the drive signal COM (the drive pulse PCOM) of the actuator 19. By feeding back the drive signal COM (the drive pulse PCOM) itself to the subtraction section 25 as the first feedback signal, and at the same time, setting forward the phase of the drive signal COM (the drive pulse PCOM) and feeding it back to the subtraction section 25 as the second feedback signal, the proportional and differential feedback of the drive signal COM (the drive pulse PCOM) becomes possible. Thus it becomes possible to sufficiently compensate the waveform of the drive signal COM (the drive pulse PCOM), and printing with high accuracy becomes possible.

By coupling the grounded resistor R as the current detector to the capacitor C of the low pass filter 28, and feeding back the output of the grounded resistor R as the current detector to the subtraction section 25 as the second feedback signal, the current of the capacitor C of the low pass filter 28 having the phase leading the phase of the drive signal COM (the drive pulse PCOM) composed of the voltage signal to the subtraction section 25 as the second feedback signal. Therefore, it becomes possible to feed back the appropriate second feedback signal with a simple configuration.

By constituting the modulator 26 with the comparison section 32 for comparing the differential signal Diff from the subtraction section 25 and the triangular wave signal with each other to thereby convert the differential signal Diff into the modulated signal PWM, it becomes possible to put embodiments of the invention into practice with a simple configuration.

Other examples will hereinafter be described. In the following discussion of other examples, the same constituents as in the first specific example are denoted with the same reference numerals as in the first example, and the explanation therefor will be omitted.

Figure 12:
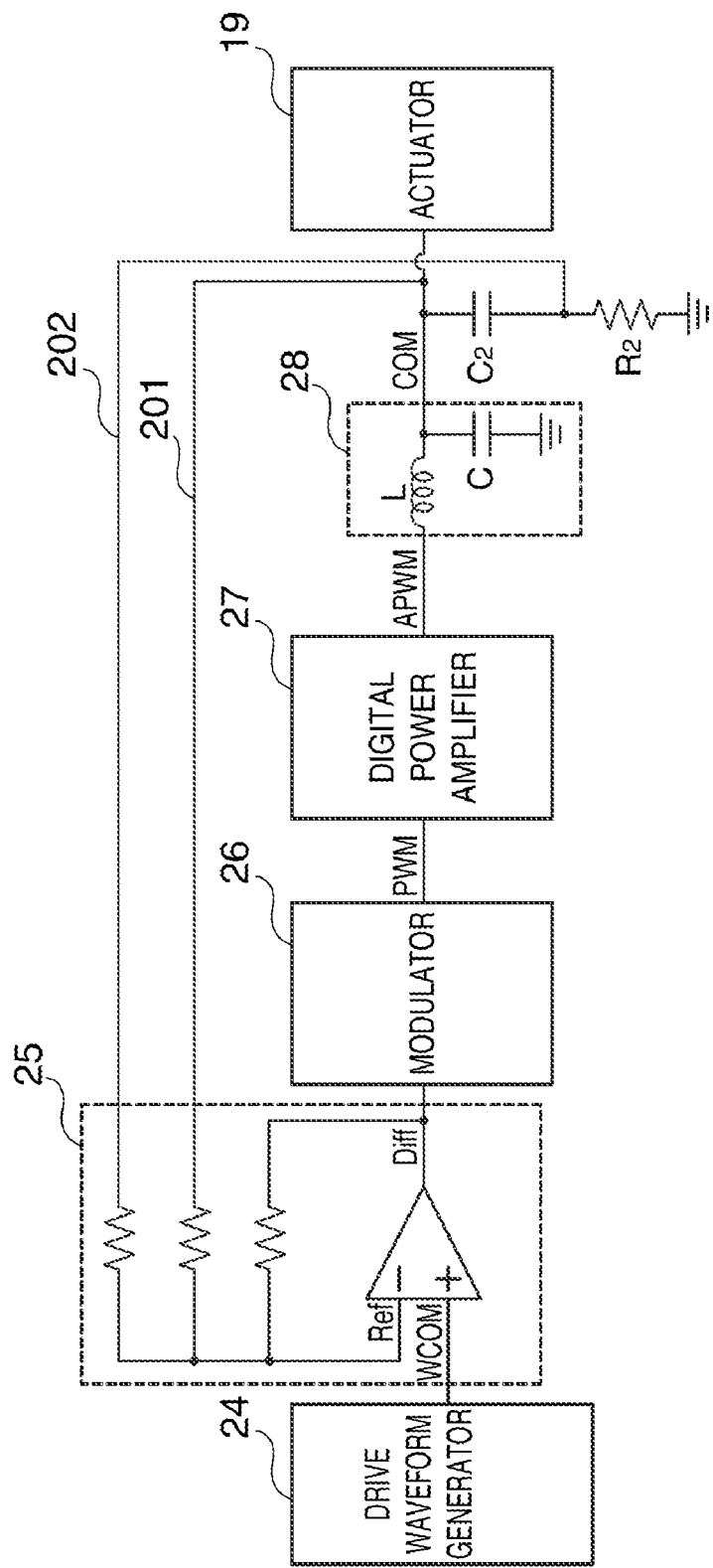
FIG. 12 is a block diagram showing a second example of the actuator drive circuit.

FIG. 12 shows a second example of the actuator drive circuit. In the first example, the current of the capacitor C of the low pass filter 28 is directly detected by the grounded resistor R as the current detector. In the present example, a second capacitor C2 is connected to the capacitor C of the low pass filter 28 in parallel. The current of the capacitor C2 is detected by a second grounded resistor R2 as a current detector. The output of the current detector is used as the second feedback signal. Also in this case, since what should be detected is the current of the capacitor C of the low pass filter 28 with the phase leading the phase of the drive signal COM (the drive pulse signal PCOM), if, for example, the product value of the capacity of the capacitor C and the resistance value of the grounded resistor R shown in FIG. 6 in the first specific example and the product value of the capacity of the second capacitor C2 and the resistance value of the second grounded resistor R2 have the same value, the current value of the second capacitor C2 is equal to the current value of the capacitor C of the low pass filter 28. On this occasion, by making the capacity of the second capacitor C2 smaller than the capacity of the capacitor C of the low pass filter 28, namely by increasing the impedance, the power consumption of the second grounded resistor R2 can be reduced. By reducing the capacity of the second capacitor C2, the resistance value of the second grounded resistor R2, as the current detector, becomes relatively large, and therefore, the equivalent series resistor of the second capacitor C2 can be neglected, thus the design becomes simple.

In the capacitive load driving device and the inkjet printer according to the present embodiment, the second capacitor C2 having a capacity smaller than that of the capacitor C of the low pass filter 28 is coupled to the output side of the low pass filter 28. The grounded resistor R2 is coupled to the second capacitor C2 as the current detector for detecting the current of the capacitor C of the low pass filter 28. The output of the grounded resistor R2 as the current detector coupled to the second capacitor C2 is fed back to the subtraction section 25 as the second feedback signal. Thus, the current of the capacitor C of the low pass filter 28 having the phase leading the phase of the drive signal COM (the drive pulse PCOM) composed of the voltage signal can be fed back to the subtraction section 25 as the second feedback signal. Therefore, the appropriate second feedback signal can be fed back, and by using the second capacitor C2 having the small capacity, namely the large impedance, the power loss is reduced, and the resistance value of the grounded resistor R2 as the current detector is increased. Therefore, the equivalent series resistor can be neglected, and the design becomes easy.

Figure 13:
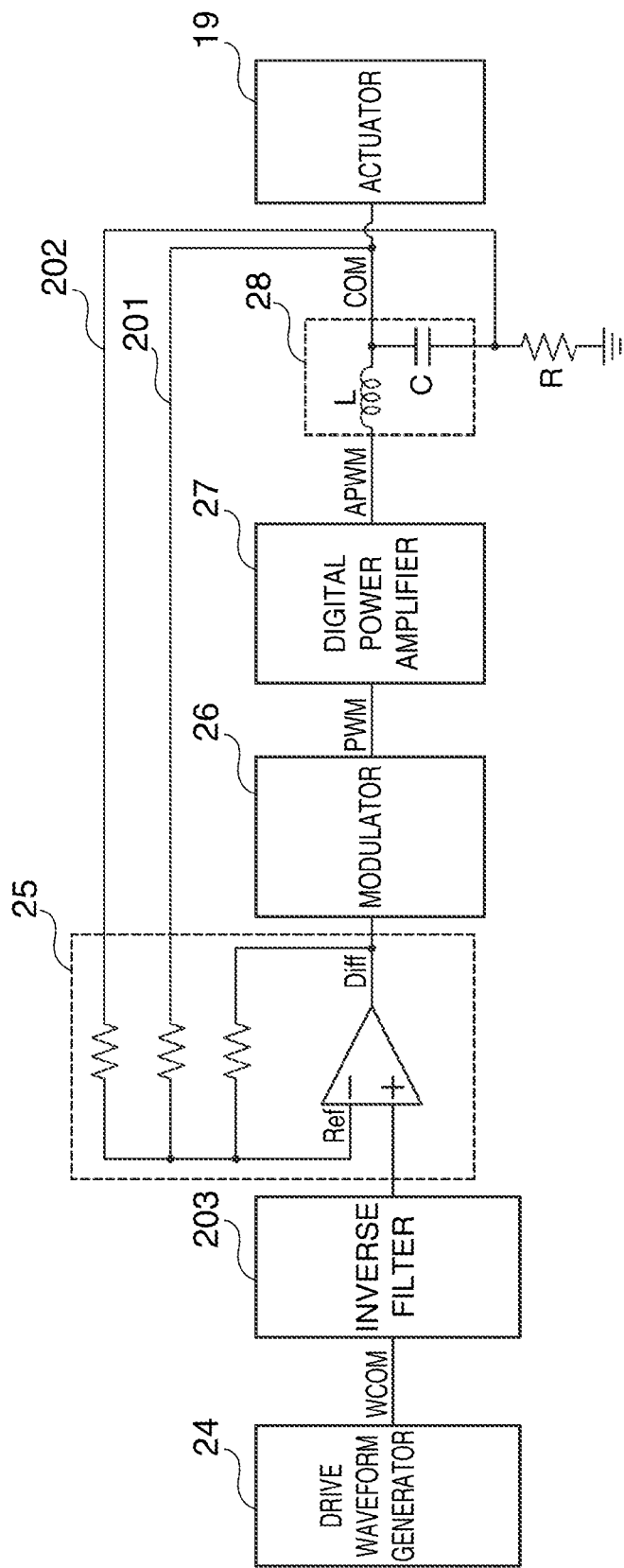
FIG. 13 is a block diagram showing a third example of the actuator drive circuit.

FIG. 13 shows a third example of the actuator drive circuit. In the present example, an inverse filter 203 is inserted between the drive waveform generator 24 and the subtraction section 25 in the actuator drive circuit according to the first example. The inverse filter 203 has a property capable of obtaining the desired drive signal COM (the drive pulse PCOM) even in the case in which, for example, the frequency characteristics of the filter composed of the low pass filter 28 and the capacitances of the actuators 19 vary in accordance with the number of actuators 19 to be driven. In the present embodiment, there is a tendency that the larger the number of actuators 19 to be driven is, the lower the gain in the high frequency band becomes. Therefore, in the case, for example, in which the frequency characteristics of the filter composed of the low pass filter 28 and the capacitance of one actuator 19 is set so that the designed waveform of the drive signal COM (the drive pulse PCOM) is obtained if the number of actuators 19 to be driven is minimized, namely one, the drive waveform signal WCOM is corrected by the inverse filter 203 so as to emphasize the component to be attenuated due to decrease in gain in accordance with the number of actuators 19 to be driven. It should be noted that the setting method of the inverse filter 203 is described in detail in WO2007/083669, which is incorporated by reference in its entirety.

Figure 14A:
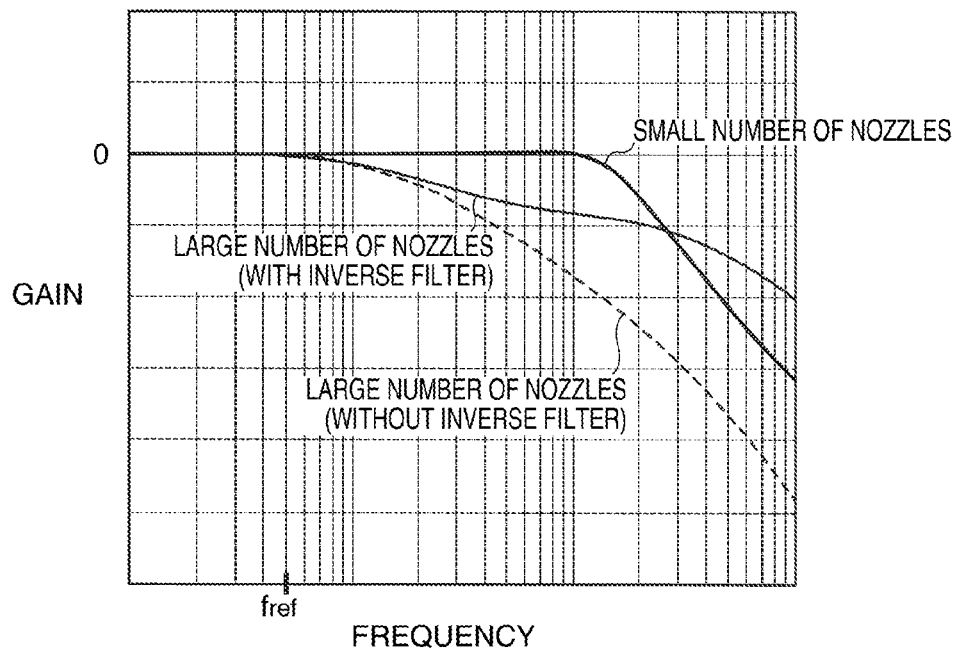
FIGS. 14A and 14B are illustrative diagrams of the action of the drive circuit shown in FIG. 13, where
Figure 14B:
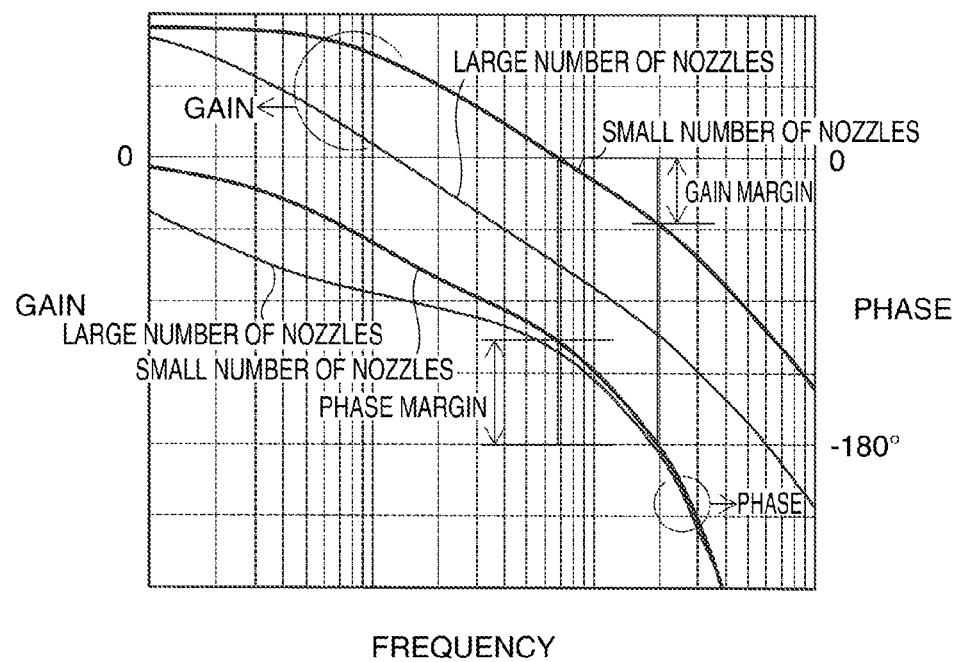

Although it is possible to roughly correct the drive waveform signal WCOM with the inverse filter 203 as described above, it is not achievable to completely cover the frequency characteristics of the filter composed of the low pass filter 28 and the capacitances of the actuators 19, which vary in accordance with the number of actuators 19 to be driven. Therefore, further compensation of the drive signal COM (the drive pulse PCOM) is provided by the inverse filter 203, and the first feedback signal and the second feedback signal described above. FIGS. 14A and 14B show the frequency characteristics of the present example.

FIG. 14A shows the frequency characteristics of the filter composed of the low pass filter 28 and the capacitances of the actuators 19. The gain in the case in which the number of driven actuators is large to the gain in the case in which the number of driven actuators is small can be approximated. By previously correcting the drive waveform signal WCOM in accordance with the number of driven actuators, the amount of compensation in particular by the first feedback signal can be reduced. In the open-loop characteristics shown in FIG. 14B, both the gain margin and the phase margin increase, and thus, further stabilization is achieved.

In the capacitive load driving device and the inkjet printer according to the present embodiment, the inverse filter 203 capable of obtaining the desired drive signal COM (the drive pulse PCOM) even in the case in which the frequency characteristics of the filter composed of the low pass filter 28 and the capacitances of the actuators 19 vary in accordance with the number of actuators 19 to be driven is inserted between the drive waveform generator 24 and the subtraction section 25. Thus, by correcting the drive waveform signal WCOM with the inverse filter 203 in accordance with the number of actuators 19 to be driven, the compensation of the drive signal COM (the drive pulse PCOM) by the first feedback signal can be reduced, and the gain margin and the phase margin of the open-loop characteristics in the path from the subtraction section 25 to the drive signal COM (the drive pulse PCOM) can be increased to thereby stabilize the system.

Figure 15:
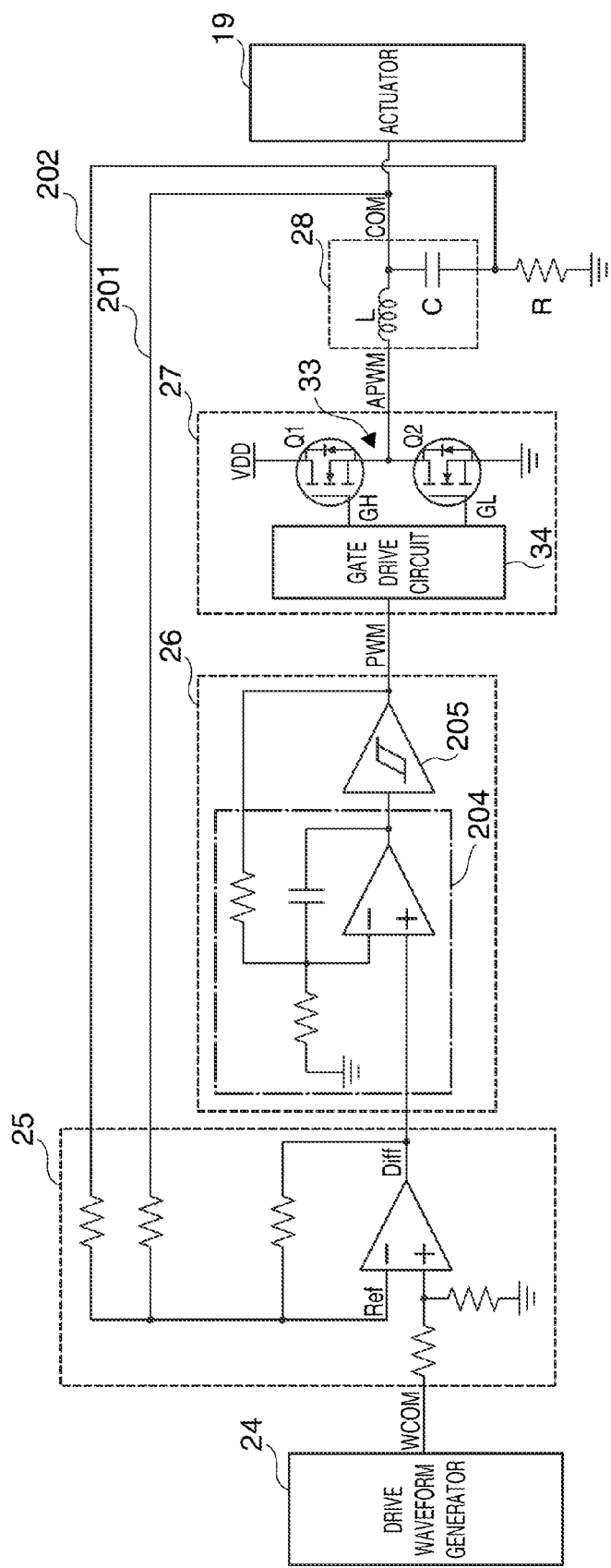
FIG. 15 is a block diagram showing a fourth example of the actuator drive circuit.

FIG. 15 shows a fourth example of the actuator drive circuit according to the present embodiment. In the present example, an integrator 204 (an integration section) is used in the modulator 26 to thereby form a so-called self-oscillation pulse width modulator for comparing the output of the integrator 204 with high and low regulation values by a comparator 205 and outputting the pulse width modulated signal PWM. In the present example, the modulated signal PWM as the output of the modulator 26 is fed back to the integrator 204. By setting the integrator 204 so as to integrate the difference value between the differential signal Diff and the modulated signal PWM, the waveform accuracy of the drive signal COM (the drive pulse PCOM) can be improved.

In the capacitive load driving device and the inkjet printer according to the present embodiment, the modulator 26 is provided with the integrator 204 and the comparator 205 for converting the output of the integrator 204 into the modulated signal PWM. The modulator 26 is configured so that the integrator 204 integrates the difference between the differential signal Diff of the subtraction section 25 and the modulated signal PWM, and then outputs the result, thereby improving the waveform accuracy of the drive signal COM (the drive pulse PCOM).

Figure 16:
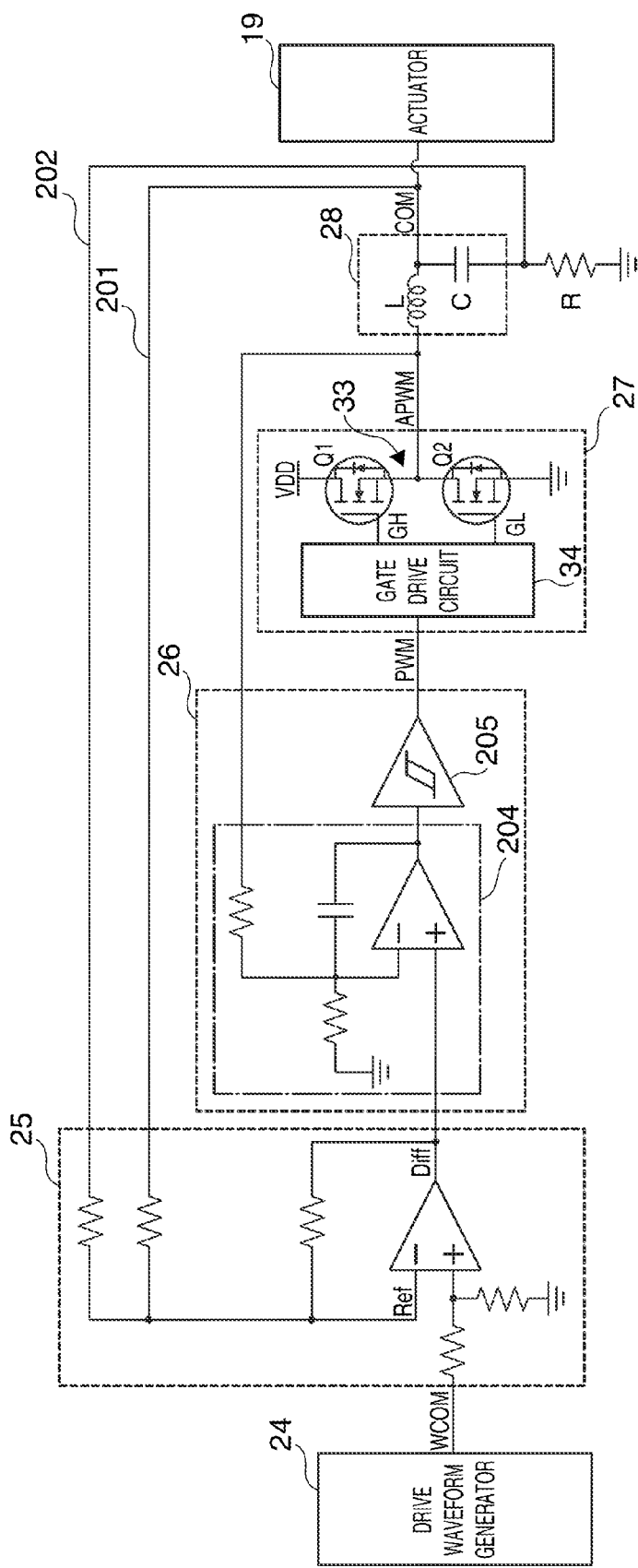
FIG. 16 is a block diagram showing a fifth example of the actuator drive circuit.

FIG. 16 shows a fifth example of the actuator drive circuit according to the present embodiment. Also in the present example, similar to the fourth example described above, the integrator 204 (the integration section) is used in the modulator 26 to thereby form a self-oscillation pulse width modulator for comparing the output of the integrator 204 with high and low regulation values by the comparator 205 and outputting the pulse width modulated signal PWM. The amplified digital signal APWM, which is the output of the digital power amplifier 27, is fed back to the integrator 204. The integrator 204 is set so as to integrate the difference value between the differential signal Diff and the amplified digital signal APWM. Since the amplified digital signal APWM does not have the phase-lag with respect to the drive signal COM (the drive pulse PCOM), the system is further stabilized, and it becomes possible to compensate the amplified digital signal APWM, which varies in accordance with the variation in the power supply voltage VDD. Thus, the waveform accuracy of the drive signal COM (the drive pulse PCOM) can be assured despite the variation in the power supply voltage VDD.

In the capacitive load driving device and the inkjet printer according to the present embodiment, the modulator 26 is provided with the integrator 204 and converts the output of the integrator 204 into the modulated signal PWM. The modulator 26 is configured so that the integrator 204 integrates the difference between the differential signal Diff of the subtraction section 25 and the amplified digital signal APWM, and then outputs the result. Thus, the system is further stabilized by feeding back the amplified digital signal APWM having no phase-lag, and at the same time, the variation in the power supply voltage VDD to the digital power amplifier 27 can be compensated.

Figure 17:
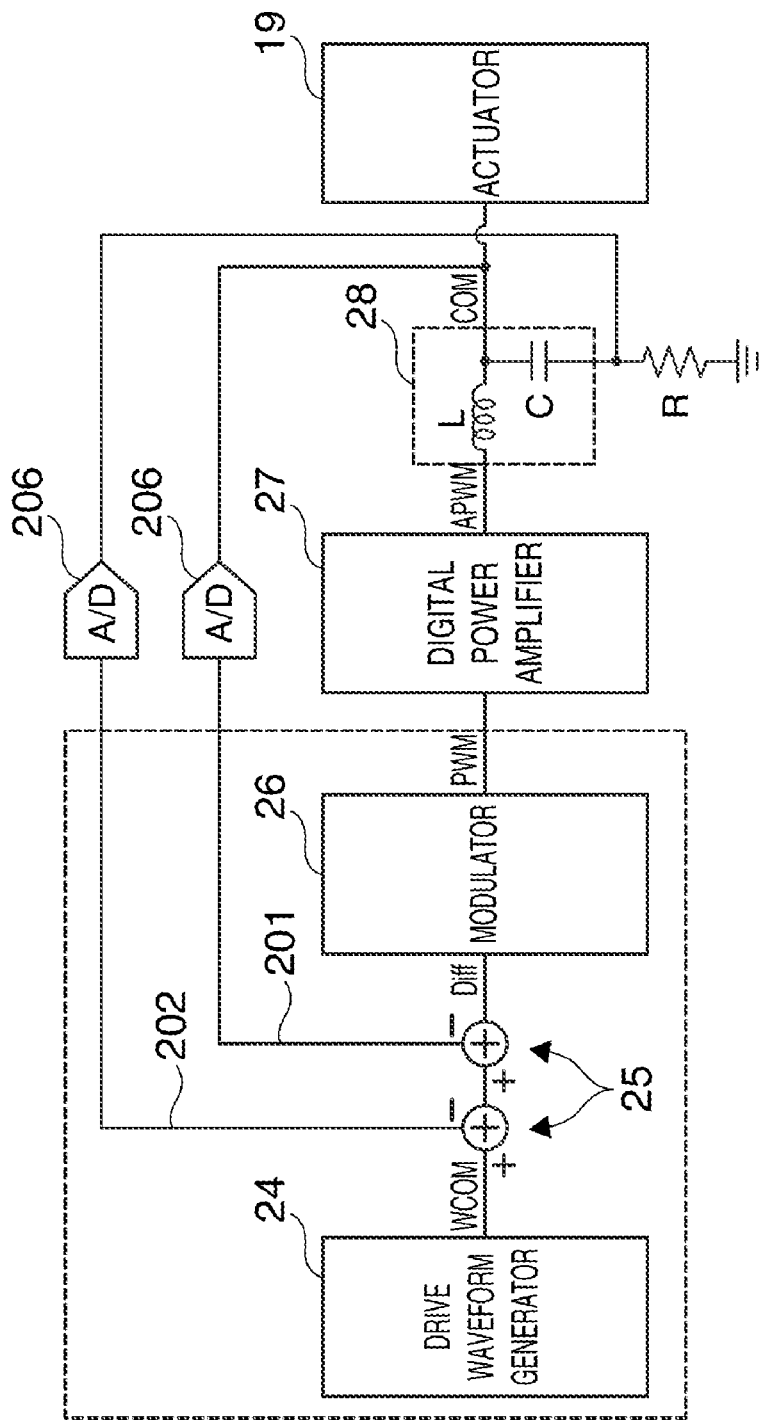
FIG. 17 is a block diagram showing a sixth example of the actuator drive circuit.

FIG. 17 shows a sixth example of the actuator drive circuit according to the present embodiment. In the present example, as described above, the portion from the drive waveform generator 24 to the modulator 26 may be built by arithmetic processing. Specifically, the portion may be built by a program in the control section 13 of the control device 11 shown in FIG. 3. It should be noted that hereinafter in the present embodiment, the portion from the drive waveform generator 24 to the modulator 26 may be built by the arithmetic processing in either example. Although the configuration of the first feedback circuit 201 and the second feedback circuit 202 shown in FIG. 17 is substantially the same as that of the first example, an analog-digital converter (an A/D converter) 206 for digitalization necessary for the arithmetic processing is inserted in each of the circuits. In the first feedback circuit 201, the drive signal COM (the drive pulse PCOM) is converted into a digital value and then fed back to the subtraction section 25. The subtraction section 25 subtracts the digital value from the drive waveform signal WCOM to obtain a subtraction value, and then further subtracts the digital value of the current value of the capacitor C of the low pass filter 28 fed back from the second feedback circuit 202 from the subtraction value to obtain a subtraction value. Then the subtraction value is input to the modulator 26 as the differential signal Diff. The modulator 26 is also configured by a program using digital values, and performs the pulse modulation on the differential signal Diff described above to output the modulated signal PWM. As described above, by digitalizing the portion from the drive waveform generator 24 to the modulator 26, the circuit configuration can be simplified.

Figure 18:
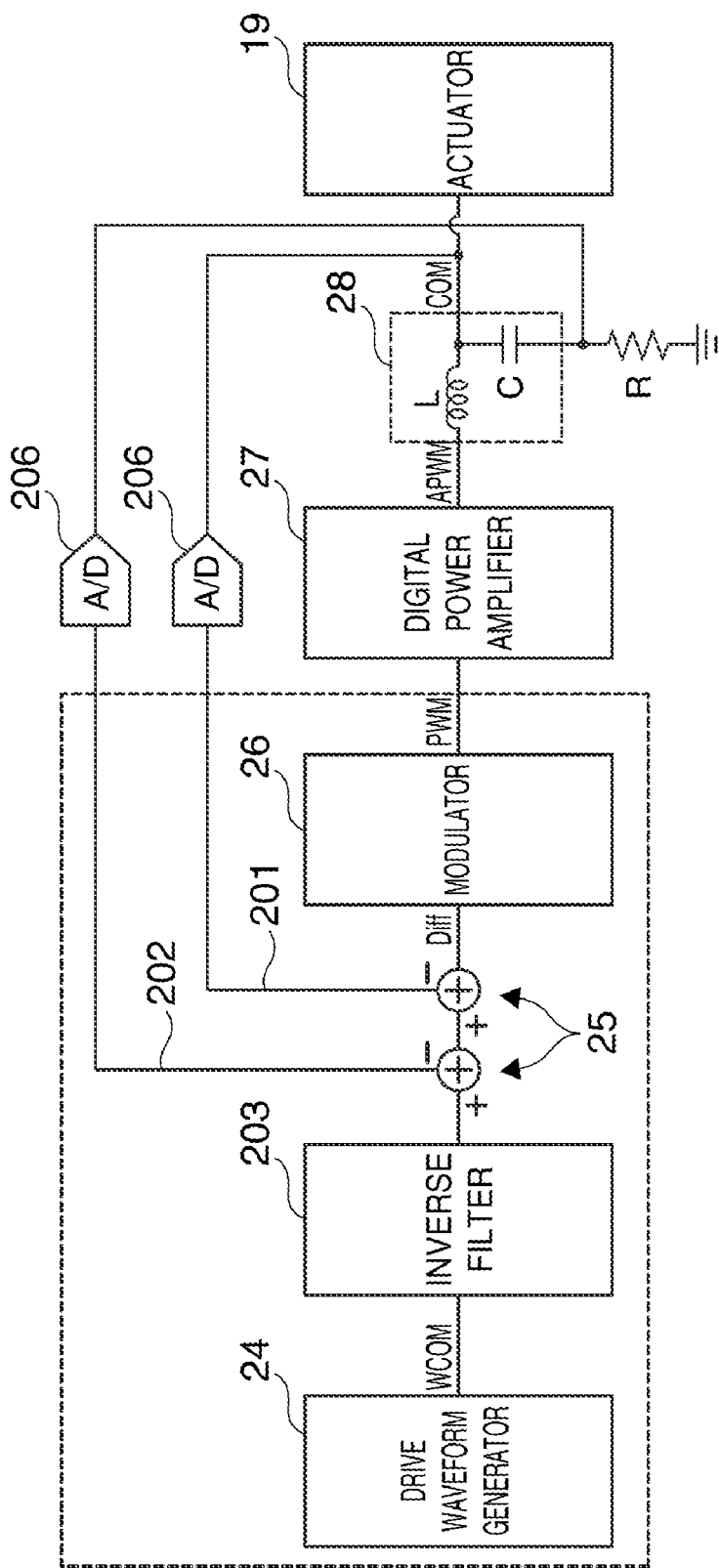
FIG. 18 is a block diagram showing a seventh example of the actuator drive circuit.

FIG. 18 shows a seventh example of the actuator drive circuit according to the present embodiment. In the present example, the inverse filter 203 described above is inserted between the drive waveform generator 24 and the subtraction section 25 in the actuator drive circuit according to the sixth example shown in FIG. 17 described above. The method of building the inverse filter 203 by programming is also described in detail in WO2007/083669 mentioned above. In the actuator drive circuit according to the present specific example, both of the advantages of the third example and the sixth example can be obtained.

Figure 19:
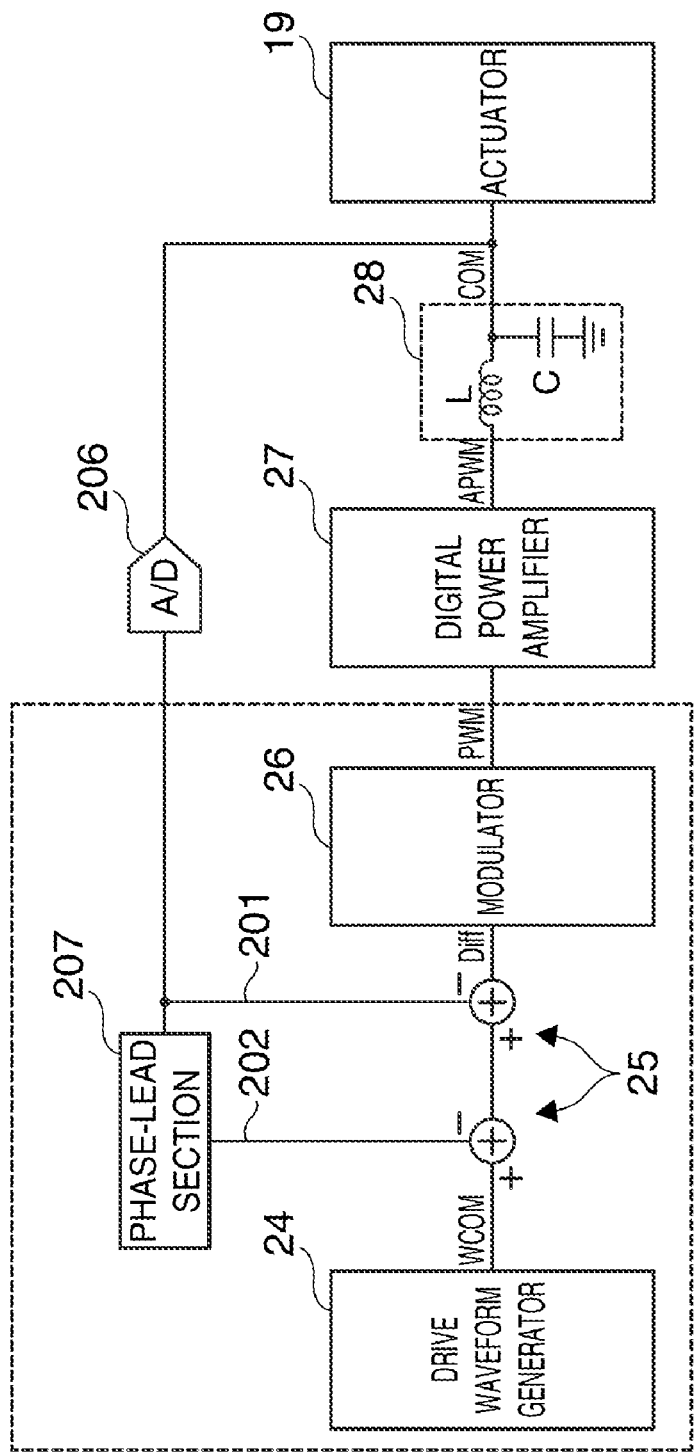
FIG. 19 is a block diagram showing an eighth example of the actuator drive circuit.

FIG. 19 shows an eighth example of the actuator drive circuit according to the present embodiment. In the present specific example, the drive signal COM (the drive pulse PCOM) only is fed back, and the drive signal COM (the drive pulse PCOM) is converted by the A/D converter 206 into a digital value. The process of feeding back the drive signal COM (the drive pulse PCOM) thus converted into the digital value directly to the subtraction section 25 as the first feedback signal corresponds to the first feedback circuit 201. On the other hand, the process of setting forward or advancing the phase of the drive signal COM (the drive pulse PCOM) thus converted into the digital value is accomplished using a phase-lead section 207 Then feeding back the signal to the subtraction section 25 as the second feedback signal corresponds to the second feedback circuit 202. According to the actuator drive circuit of the present example, the substantial circuit configuration can further be simplified.

Figure 20:
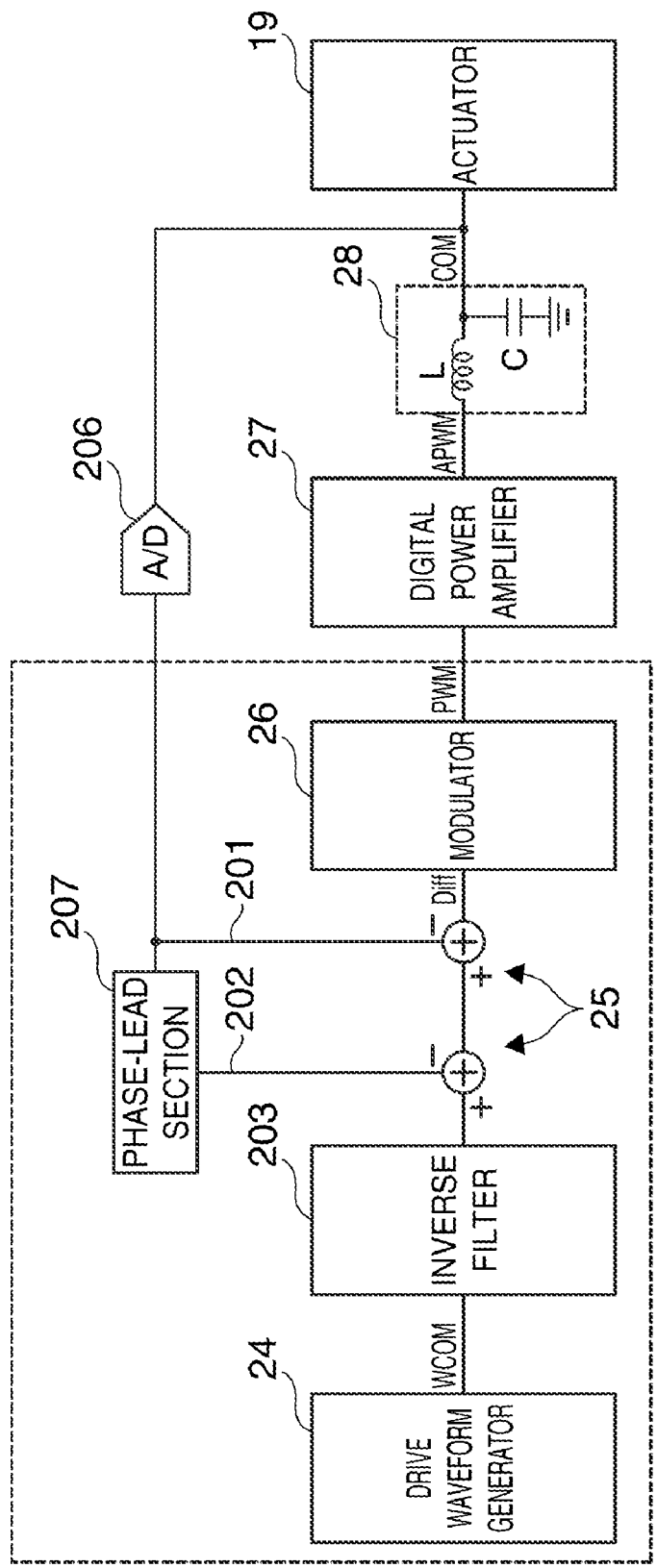
FIG. 20 is a block diagram showing a ninth example of the actuator drive circuit.

FIG. 20 shows a ninth example of the actuator drive circuit according to the present embodiment. In the present specific example, the inverse filter 203 described above is inserted between the drive waveform generator 24 and the subtraction section 25 in the actuator drive circuit according to the eighth example shown in FIG. 19 described above. In the actuator drive circuit according to the present specific example, both of the advantages of the third example and the eighth example can be obtained.

It should be noted that although in the present embodiments described above only the case in which the capacitive load driving device is applied to the line head-type inkjet printer is described in detail, the capacitive load driving device according to the invention can also be applied to multi-pass type inkjet printer in a similar manner.

Then, as a second embodiment of the invention, a capacitive load driving device applied to a fluid ejection device will be explained. In the following explanation of the embodiment, the same constituents as in the first embodiment are denoted with the same reference numerals as in the first embodiment, and the explanation therefor will be omitted.

Figure 21:
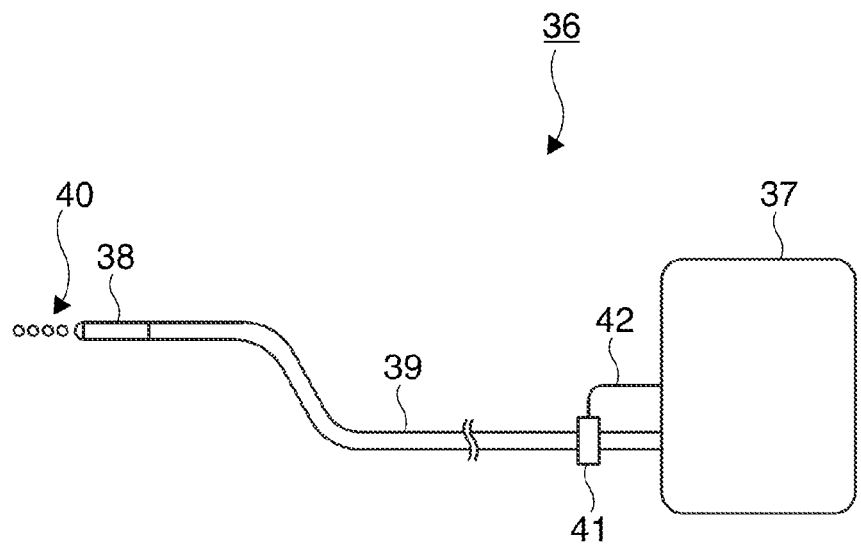
FIG. 21 is a schematic configuration diagram illustrating a second embodiment of a fluid ejection device using the capacitive load driving device

FIG. 21 is an illustrative diagram showing an example of a schematic configuration of a fluid ejection device according to the present embodiment. The fluid ejection device according to the present embodiment can be adapted for various purposes such as cleaning fine objects and structures, and as a surgical knife. In the embodiment explained hereinafter, the disclosure illustrates that the fluid ejection device is suitable to be disposed at the tip of a catheter used for the purpose of removing a blood clot or the like. The fluid ejection device may also be suitable for incising or excising body tissue as an example. Therefore, the fluid used in these embodiments may be water or saline. These are hereinafter collectively described as and are examples of a fluid.

In FIG. 21, the fluid ejection device 36 is provided with a fluid ejection control section 37 including a pump as a fluid supply section for supplying a fluid at a constant pressure, a fluid ejection section 38 for changing the fluid to pulsation, and a tube 39 communicating between the fluid ejection control section 37 and the fluid ejection section 38 as basic constituents. The fluid ejection section 38 changes the fluid into the pulsation and then ejects the fluid as a droplet 40 at high speed in a pulsed manner. As described later, a piezoelectric element formed of a capacitive load may be disposed inside the fluid ejection section 38 as an actuator, connecting wires for inputting the drive signal are connected to the piezoelectric element, and the connecting wires are inserted in a tube 39. The connecting wires are branched by the branch section 41 from the tube 39 in the vicinity or inside of the fluid ejection control section 37, and are connected to the drive circuit section of the fluid ejection control section 37 as the connection wiring lines 42. The tube 39 is connected to the pump included in the fluid ejection control section 37.

Figure 22:
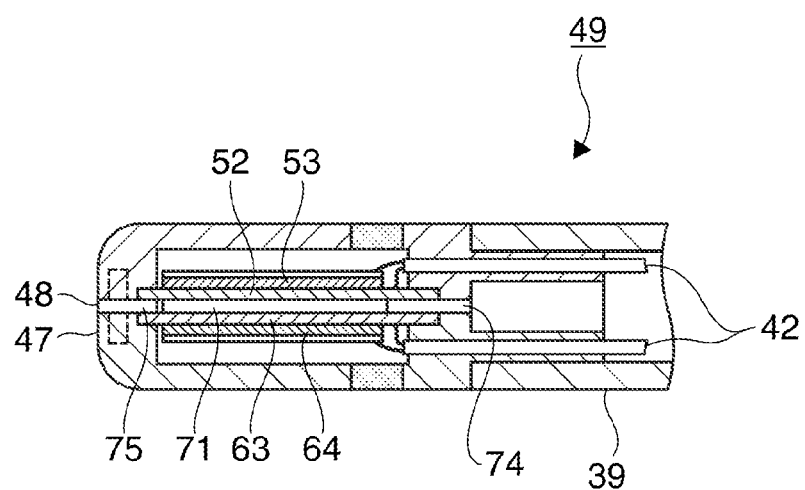
FIG. 22 is a cross-sectional view of the fluid ejection section shown in FIG. 21.

Subsequently, the configuration of the fluid ejection section 38 will be explained with reference to FIG. 22. FIG. 22 is a vertical cross-sectional view of the fluid ejection section 38. At the tip portion 47 of the fluid ejection section 38 a fluid ejection opening section 48 for ejecting the fluid is opened, and the tube 39 having flexibility is fitted at the base portion 49. Inside the fluid ejection section 38, a fluid chamber 71 having walls partially formed of diaphragms 52, 63 is disposed. The fluid chamber 71 is connected to the fluid ejection opening 48 via an exit channel 75. The fluid chamber 71 is also connected to the tube 39 via an entrance channel 74. Piezoelectric elements 53, 64 are bonded respectively to the diaphragms 52, 63. When the drive signal is input to the piezoelectric elements 53, 64, the diaphragm is deformed due to expansion and contraction of the piezoelectric elements 53, 64 to thereby change the capacity of the fluid chamber 71.

Subsequently, the flow of the fluid of the fluid ejection device 36 will be explained with reference to FIGS. 21 and 22. The fluid ejection control section 37 is provided with a fluid container not shown and a pump connected to the fluid container. The pump feeds the fluid to the tube 39. The fluid contained in the fluid container is supplied by the pump to the fluid chamber 71 via the tube 39 and the entrance channel 74 at constant pressure. Here, when the drive signal is input to the piezoelectric elements 53, 64 to thereby expand or contract the piezoelectric elements 53, 64, the diaphragms 52, 63 change the capacity of the fluid chamber 71. As a result, since the pressure in the fluid chamber 71 varies, a pulsed fluid discharge occurs, namely high speed ejection of a pulsed droplet, from the fluid ejection opening section 48 via the exit channel 75.

Figure 23:
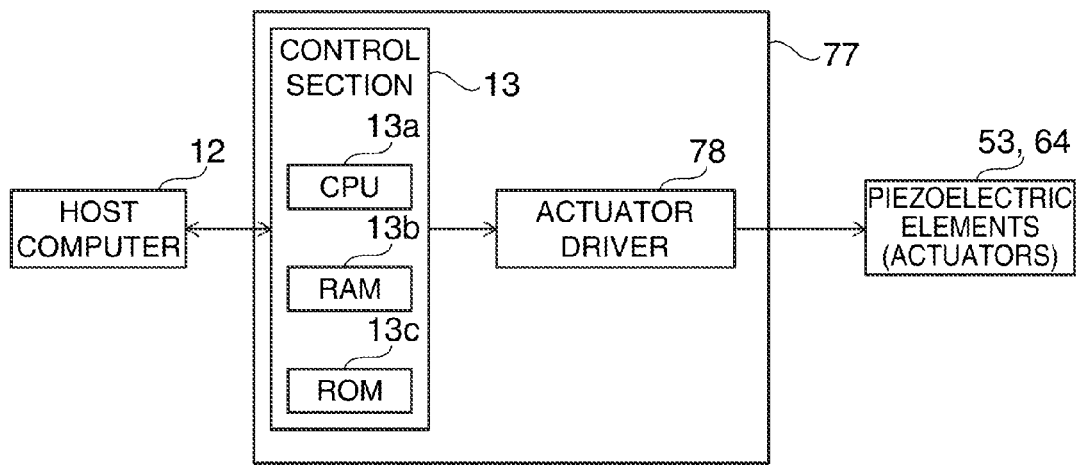
FIG. 23 is a block diagram of a control device of the fluid ejection device shown in FIG. 21.

FIG. 23 shows an actuator drive control device 77 disposed inside the fluid ejection control section 37. The actuators of the fluid ejection device according to the present embodiment are the piezoelectric elements 53, 64, and are also the capacitive loads similar to the case of the first embodiment described above. Similar to the control device of the first embodiment, the actuator drive control device 77 is configured to include the control section 13 composed of the computer system for reading input data and commands input from the host computer 12, and then executing predetermined arithmetic processing based on the input data and the commands, and an actuator driver 78 for controlling the drive of the piezoelectric elements 53, 64 in accordance with the control signal from the control section 13. The control section 13 is provided with the CPU 13a, the RAM 13b, and the ROM 13c similar to the case of the first embodiment.

Figure 24:
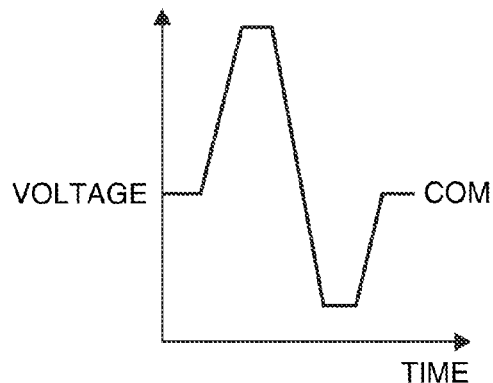
FIG. 24 is an illustrative diagram of a drive signal of an actuator composed of a capacitive load.

FIG. 24 shows an example of the drive signal COM supplied from the actuator driver 78 in the actuator drive control device 77 to the piezoelectric elements 53, 64, and for driving the actuators composed of the piezoelectric elements 53, 64. As is understood from the disclosure provided above, in such a fluid ejection device as in the present embodiment, although various types of drive signals can be used, in the present embodiment, the trapezoidal wave voltage signal varying the voltage centered on an intermediate voltage is adopted similarly to the first embodiment described above. The drive signal COM has the rising edge portion of the voltage corresponding to the stage of increasing the capacity of the fluid chamber 71 to pull in the fluid, and the falling edge portion of the voltage corresponding to the stage of reducing the capacity of the fluid chamber 71 to push out the fluid.

Therefore, the actuator drive circuits according to the first through ninth examples described above can directly be used as the actuator drive circuit built in the actuator driver 78 while replacing the actuators with the piezoelectric elements 53, 64. In this example, the resonance of the low pass filter 28 composed of the quadratic low pass filter can effectively be attenuated by the first feedback signal and the second feedback signal as described above. In the case in which the piezoelectric elements 53, 64 having the respective capacitances different from each other are randomly connected to and driven by one actuator drive circuit, the frequency characteristics of the filter composed of the low pass filter 28 and the capacitances of the piezoelectric elements 53, 64 to be driven vary in accordance with the piezoelectric elements 53, 64 connected to the low pass filter 28, and the distortion is caused in the waveform of the drive signal COM similarly to the case of the first embodiment. In such a case, according to the actuator drive circuit of any one of the first through ninth examples of the first embodiment, the waveform distortion of the drive signal COM can be prevented. The advantages corresponding to the respective examples can similarly be obtained. Regarding the third, the seventh, and the ninth examples of the first embodiment, the drive waveform signal WCOM is corrected by the inverse filter 203 so as to emphasize the component to be attenuated due to the reduction of the gain in accordance with the capacitances of the piezoelectric elements 53, 64 to be connected.

As described above, also in the fluid ejection device using the capacitive load driving device according to the present embodiment, when applying the drive signal COM to the piezoelectric elements 53, 64 as the capacitive loads, the capacity of the fluid chamber 71 is reduced via the diaphragms 52, 63 to thereby eject the fluid in the fluid chamber 71. In this example, the pulse modulation is performed on the differential signal Diff between the drive waveform signal WCOM output from the subtraction section 25 and the two feedback signals Ref to obtain the modulated signal PWM, the power amplification is performed by the digital power amplifier 27 on the modulated signal PWM to obtain the amplified digital signal APWM, and the amplified digital signal APWM is smoothed by the low pass filter 28 to thereby obtain the drive signal COM of the piezoelectric elements 53, 64. By feeding back the drive signal COM itself to the subtraction section 25 as the first feedback signal, and at the same time, setting forward or advancing the phase of the drive signal COM and feeding it back to the subtraction section 25 as the second feedback signal, the proportional and differential feedback of the drive signal COM becomes possible. Thus it becomes possible to sufficiently compensate the waveform of the drive signal COM, and fluid ejection with high accuracy.

Then, as a third embodiment of the invention, a capacitive load driving device applied to a fluid ejection device different in type from the fluid ejection device according to the second embodiment will be explained. In the following explanation of the third embodiment, the same constituents as in the first embodiment or the second embodiment are denoted with the same reference numerals, and the explanation therefor will be omitted.

Figure 25:
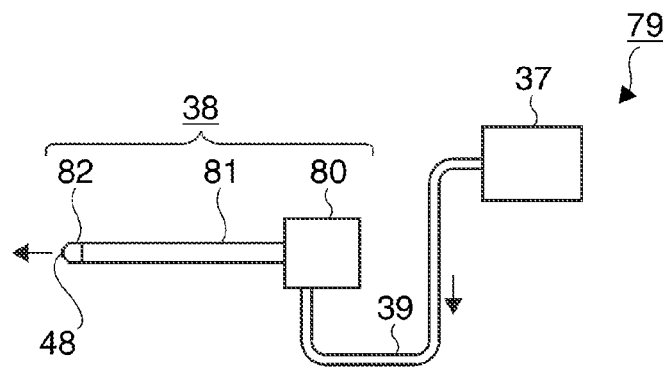
FIG. 25 is a schematic configuration diagram illustrating a third embodiment of a fluid ejection device using the capacitive load driving device.

FIG. 25 is an explanatory diagram showing an example of a schematic configuration of a fluid ejection device according to the present embodiment. The fluid ejection device according to the present embodiment can be as adapted to various applications such as cleaning a fine object and a structure, and as a surgical knife, and in the embodiment described below, the disclosure is presented illustrating that the fluid ejection device is suitable for incising or excising body tissue as an example. Therefore, the fluid used in the embodiment is water or saline, and therefore, these are hereinafter collectively described as and are examples of a fluid.

In FIG. 25, the fluid ejection system 79 is configured including the fluid ejection control section 37 including the fluid container not shown for containing the fluid, and a pump as a pressure generation section, the fluid ejection section 38 for pulsating and ejecting the fluid supplied from the pump, and the tube 39 for communicating between the fluid ejection section 38 and the pump as the basic constituents. The fluid ejection section 38 has a pulsation generation mechanism 80 for pulsating and ejecting the fluid supplied thereto at high pressure and a high frequency, and a connecting channel tube 81 connected to the pulsation generation mechanism 80, and the tip portion of the connecting channel tube 81 is provided with a nozzle 82 having a fluid ejection opening 48 with a reduced cross-sectional area of the channel.

Then, the flow of the fluid in the fluid ejection system 79 will be explained. The fluid contained in the fluid container provided to the fluid ejection control section 37 is supplied by the pump to the pulsation generation mechanism 80 via the tube 39 at constant pressure. The pulsation generation mechanism 80 is provided with a fluid chamber 71 described later, and a capacity varying section for the fluid chamber 71. The pulsation generation mechanism 80 drives the capacity varying section to generate the pulsation, thereby ejecting the fluid from the fluid ejection opening section 48 at highspeed in a pulsed manner. Detailed explanation of the pulsation generation mechanism 80 will be described later with reference to FIG. 26. It should be noted that when performing an operation using the fluid ejection system 79, the region the operator grips may be the pulsation generation mechanism 80.

Figure 26:
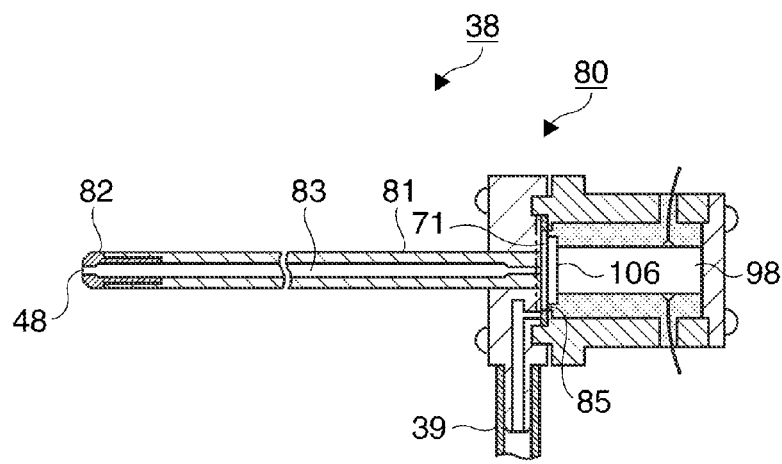
FIG. 26 is a vertical cross-sectional view illustrating a configuration of a pulsation generation mechanism illustrated in FIG. 25.

Subsequently, the configuration of the fluid ejection section 38 will be explained. FIG. 26 is a cross-sectional view of a principal configuration of the pulsation generation mechanism 80 according to the present embodiment cut along the direction of the channel of the fluid. The fluid ejection section 38 is composed of the pulsation generation mechanism 80 including a pulsation generation section of the fluid, and the connecting channel tube 81 having an exit connecting channel 83 and the nozzle 82. The pulsation generation mechanism 80 has the fluid chamber 71 inside, and a wall of the fluid chamber 71 is partially formed of a diaphragm 85. A stacked piezoelectric element 98 as the capacity varying section is fixed to the diaphragm 85 via an upper plate 106. Specifically, when the drive signal is input to the piezoelectric element 98, the diaphragm 85 is deformed due to expansion and contraction of the piezoelectric element 98 to thereby vary the capacity of the fluid chamber 71. As described above, the pulsation generation mechanism 80 is configured so as to be able to eject the fluid supplied thereto from the fluid ejection opening section 48 in a pulsed manner.

Figure 27:
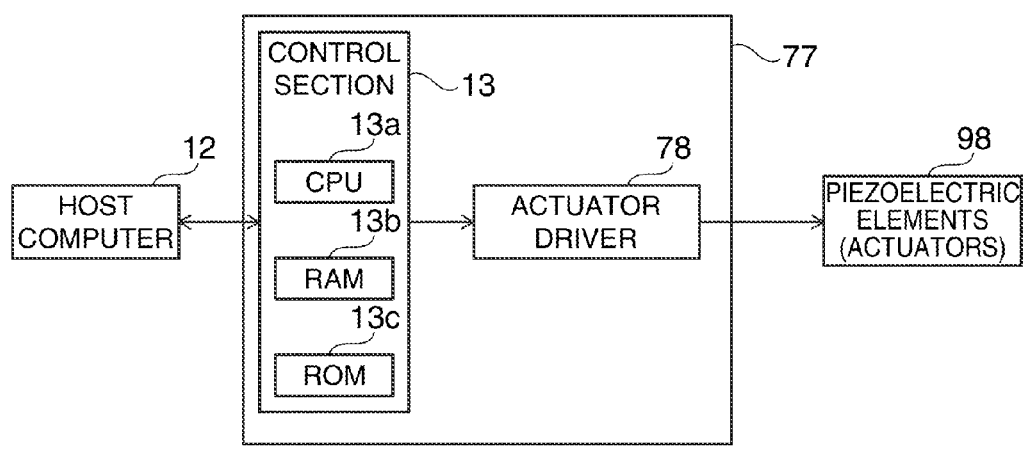
FIG. 27 is a block diagram of a control device of the fluid ejection device illustrated in FIG. 25.
Figure 28:
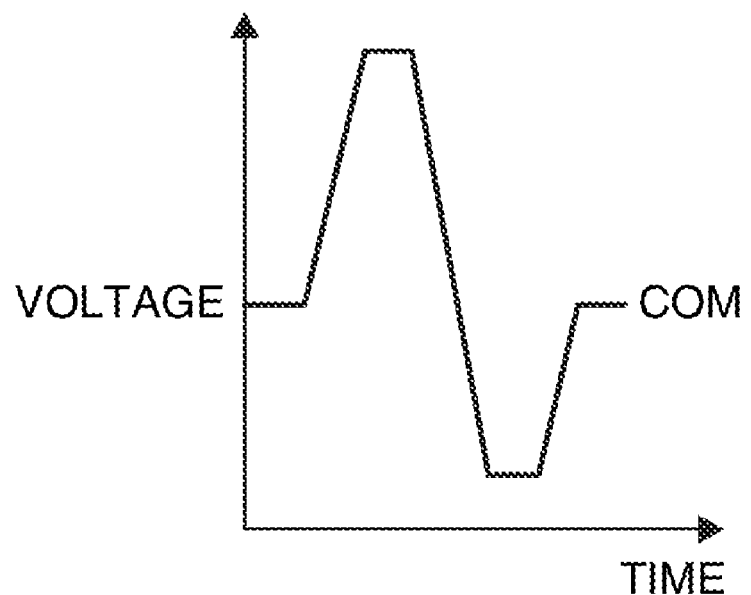
FIG. 28 is an illustrative diagram of the drive signal of the actuator composed of a capacitive load.

FIG. 27 shows an actuator drive control device 77 disposed inside the fluid ejection control section 37. The actuator of the fluid ejection device according to the present embodiment is the piezoelectric element 98, and is also the capacitive load similar to the case of the second embodiment described above. Similarly to the control device of the second embodiment, the actuator drive control device 77 is configured to include the control section 13 composed of the computer system for reading input data and commands input from the host computer 12, and then executing predetermined arithmetic processing based on the input data and the commands. The actuator drive control device 77 also includes an actuator driver 78 for controlling the drive of the piezoelectric element 98 in accordance with the control signal from the control section 13. The control section 13 is provided with the CPU 13a, the RAM 13b, and the ROM 13c similar to the case of the first and second embodiments. FIG. 28 shows an example of the drive signal COM supplied from the actuator driver 78 in the actuator drive control device 77 to the piezoelectric element 98, and for driving the actuator composed of the piezoelectric element 98. As is understood from the explanation described above, in such a fluid ejection device as in the present embodiment, although various types of drive signals can be used, in the present embodiment, the trapezoidal wave voltage signal varying the voltage centered on an intermediate voltage is adopted similarly to the second embodiment described above. The drive signal COM has the rising edge portion of the voltage corresponding to the stage of increasing the capacity of the fluid chamber 71 to pull in the fluid, and the falling edge portion of the voltage corresponding to the stage of reducing the capacity of the fluid chamber 71 to push out the fluid.

Therefore, the actuator drive circuits according to the first through ninth examples described above can directly be used as the actuator drive circuit built in the actuator driver 78 while replacing the actuator with the piezoelectric element 98. On this occasion, the resonance of the low pass filter 28 composed of the quadratic low pass filter can effectively be attenuated by the first feedback signal and the second feedback signal as described above. In the case in which the piezoelectric elements 98 having the capacitances different from each other are randomly connected to and driven by one actuator drive circuit, the frequency characteristics of the filter composed of the low pass filter 28 and the capacitances of the piezoelectric elements 98 to be driven vary in accordance with the piezoelectric elements 98 connected thereto, and the distortion is caused in the waveform of the drive signal COM similarly to the case of the first embodiment. In such a case, according to the actuator drive circuit of any one of the first through ninth examples of the first embodiment, the waveform distortion of the drive signal COM can be prevented. The advantages corresponding to the respective specific examples can similarly be obtained. Regarding the third, the seventh, and the ninth specific examples of the first embodiment, the drive waveform signal WCOM is corrected by the inverse filter 203 so as to emphasize the component to be attenuated due to the reduction of the gain in accordance with the capacitance of the piezoelectric element 98 to be connected.

As described above, also in the fluid ejection device using the capacitive load driving device according to the present embodiment, when applying the drive signal COM to the piezoelectric element 98 as the capacitive load, the capacity of the fluid chamber 71 is reduced via the diaphragms 85 to thereby eject the fluid in the fluid chamber 71. In this example, the pulse modulation is performed on the differential signal Diff between the drive waveform signal WCOM output from the subtraction section 25 and the two feedback signals Ref to obtain the modulated signal PWM, the power amplification is performed by the digital power amplifier 27 on the modulated signal PWM to obtain the amplified digital signal APWM, and the amplified digital signal APWM is smoothed by the low pass filter 28 to thereby obtain the drive signal COM of the piezoelectric element 98. By feeding back the drive signal COM itself to the subtraction section 25 as the first feedback signal, and at the same time, setting forward or advancing the phase of the drive signal COM and feeding it back to the subtraction section 25 as the second feedback signal, the proportional and differential feedback of the drive signal COM becomes possible. Thus it becomes possible to sufficiently compensate the waveform of the drive signal COM, and fluid ejection with high accuracy becomes possible.

It should be noted that the fluid ejection device using the capacitive load driving device of the invention can also be embodied as a fluid ejection device for ejecting a fluid (including a fluid like member dispersing particles of functional materials, and a fluid such as a gel besides fluids) other than the ink or the saline described above, or a fluid (e.g., a solid substance capable of flowing as a fluid and being ejected) other than liquid. The fluid ejection device can be, for example, a fluid ejection device for ejecting a fluid including a material such as an electrode material or a color material used for manufacturing a liquid crystal display, an electroluminescence (EL) display, a plane emission display, or a color filter in a form of a dispersion or a solution, a fluid ejection device for ejecting a living organic material used for manufacturing a biochip, or a fluid ejection device used as a precision pipette for ejecting a fluid to be a sample. Further, the fluid ejection device can be a fluid ejection device for ejecting lubricating oil to a precision machine such as a timepiece or a camera in a pinpoint manner, a fluid ejection device for ejecting on a substrate a fluid of transparent resin such as ultraviolet curing resin for forming a fine hemispherical lens (an optical lens) used for an optical communication device. Further, the fluid ejection device can be a fluid ejection device for ejecting an etching fluid of an acid or an alkali for etching a substrate or the like, a fluid ejection device for ejecting a gel, or a fluid ejection recording apparatus for ejecting a solid substance including fine particles such as a toner as an example. Embodiments of the invention can be applied to either one of these ejection devices.

What is claimed is:

1. A capacitive load driving device comprising:
   a drive waveform generator that is adapted to generate a drive waveform signal;
   a subtraction section that is adapted to output a differential signal between the drive waveform signal and one of a first feedback signal and a second feedback signals;
   a modulator that is adapted to obtain a modulated signal by perform pulse modulation on the differential signals;
   a digital power amplifier that is adapted to obtain an amplified digital signal by power-amplify the modulated signal;
   a low pass filter that includes an inductor and a capacitor, the low pass filter being adapted to smooth the amplified digital signal to obtain a drive signal of a capacitive load;
   a first feedback circuit that is adapted to feed back the drive signal to the subtraction section as the first feedback signal; and
   a second feedback circuit that is adapted to set forward a phase of the drive signal and to feed back the drive signal with the set forward phase to the subtraction section as the second feedback signal.

2. The capacitive load driving device according to claim 1, further comprising:
   a current detector connected to the capacitor of the low pass filter,
   wherein the second feedback circuit feeds back an output of the current detector to the subtraction section as the second feedback signal.

3. A fluid ejection device comprising:
   the capacitive load driving device according to claim 2; and
   an actuator as the capacitive load,
   wherein the capacitive load driving device drives the actuator to eject a fluid.

4. The capacitive load driving device according to claim 1, further comprising:
   a second capacitor to be connected to an output side of the low pass filter and having a capacity smaller than a capacity of the capacitor of the low pass filter; and
   a current detector connected to the second capacitor,
   wherein the second feedback circuit feeds back an output of the current detector to the subtraction section as the second feedback signal.

5. A fluid ejection device comprising:
   the capacitive load driving device according to claim 4; and
   an actuator as the capacitive load,
   wherein the capacitive load driving device drives the actuator to eject a fluid.

6. The capacitive load driving device according to claim 1, further comprising:
   an inverse filter intervening between the drive waveform generator and the subtraction section, the inverse filter capable of obtaining a desired drive signal even in a case in which frequency characteristics of a capacitance of the low pass filter and the capacitive load vary in accordance with a number of capacitive loads to be driven.

7. A fluid ejection device comprising:
   the capacitive load driving device according to claim 6; and
   an actuator as the capacitive load,
   wherein the capacitive load driving device drives the actuator to eject a fluid.

8. The capacitive load driving device according to claim 1, wherein
   the modulator is provided with a comparison section adapted to compare the differential signal of the subtraction section and a triangular wave signal to convert the drive signal into the modulated signal.

9. A fluid ejection device comprising:
   the capacitive load driving device according to claim 8; and
   an actuator as the capacitive load,
   wherein the capacitive load driving device drives the actuator to eject a fluid.

10. The capacitive load driving device according to claim 1, wherein
    the modulator is provided with an integration section and a comparison section adapted to convert an output of the integration section into the modulated signal, wherein the integration section integrates a difference between the differential signal of the subtraction section and the modulated signal, and then outputs a result of the integration.

11. A fluid ejection device comprising:
    the capacitive load driving device according to claim 10; and
    an actuator as the capacitive load,
    wherein the capacitive load driving device drives the actuator to eject a fluid.

12. The capacitive load driving device according to claim 1, wherein
    the modulator is provided with an integration section and a comparison section adapted to convert an output of the integration section into the modulated signal, wherein the integration section integrates a difference between the differential signal of the subtraction section and the amplified digital signal, and then outputs a result of the integration.

13. A fluid ejection device comprising:
    the capacitive load driving device according to claim 12; and
    an actuator as the capacitive load,
    wherein the capacitive load driving device drives the actuator to eject a fluid.

14. A fluid ejection device comprising:
    the capacitive load driving device according to claim 1; and
    an actuator as the capacitive load,
    wherein the capacitive load driving device drives the actuator to eject a fluid.

15. The capacitive load driving device according to claim 1,
    wherein the modulated signal is PWM signal of PDM signal 16. A fluid ejection device comprising:
    the capacitive load driving device according to claim 15; and
    an actuator as the capacitive load
    wherein the capacitive load driving device drives the actuator to eject a fluid.

* * * * *